United States Patent
Kohr

(10) Patent No.: US 7,906,304 B2
(45) Date of Patent: Mar. 15, 2011

(54) METHOD AND BIOREACTOR FOR PRODUCING SYNFUEL FROM CARBONACEOUS MATERIAL

(75) Inventor: William J. Kohr, Davis, CA (US)

(73) Assignee: GeoSynFuels, LLC, Golden, CO (US)

( * ) Notice: Subject to any disclaimer, the term of this patent is extended or adjusted under 35 U.S.C. 154(b) by 266 days.

(21) Appl. No.: 11/100,348

(22) Filed: Apr. 5, 2005

(65) Prior Publication Data
US 2006/0223154 A1    Oct. 5, 2006

(51) Int. Cl.
C12P 5/00      (2006.01)
C12P 5/02      (2006.01)
C12P 1/00      (2006.01)
C02F 3/34      (2006.01)
C12S 3/00      (2006.01)

(52) U.S. Cl. ......... 435/166; 435/167; 435/262; 435/267
(58) Field of Classification Search ................. 435/166, 435/262
See application file for complete search history.

(56) References Cited

U.S. PATENT DOCUMENTS

| | | |
|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Shmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,185,216 A | 5/1965 | Hitzman |
| 3,332,487 A | 7/1967 | Jones |
| 3,340,930 A | 9/1967 | Hitzman |
| 3,724,542 A | 4/1973 | Hamilton |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wiberger et al. |
| 4,349,633 A | 9/1982 | Worne et al. |
| 4,358,537 A | 11/1982 | Chynoweth |
| RE31,347 E | 8/1983 | Reijonen et al. |
| 4,416,332 A | 11/1983 | Wiberger et al. |
| 4,446,919 A | 5/1984 | Hitzman |
| 4,450,908 A | 5/1984 | Hitzman |
| 4,475,590 A | 10/1984 | Brown |
| 4,518,399 A | 5/1985 | Croskell et al. |
| 4,522,261 A | 6/1985 | McInerney et al. |
| 4,610,302 A | 9/1986 | Clark |
| 4,640,767 A | 2/1987 | Zajic et al. |
| 4,678,033 A | 7/1987 | Killough |
| 4,799,545 A | 1/1989 | Silver et al. |
| 4,826,769 A | 5/1989 | Menger |
| 4,845,034 A | 7/1989 | Menger et al. |
| 4,883,753 A | 11/1989 | Belaich et al. |
| 4,905,761 A | 3/1990 | Bryant |
| 4,936,996 A | 6/1990 | Messing |
| 4,947,932 A | 8/1990 | Silver et al. |
| 4,971,151 A | 11/1990 | Sheehy |
| 5,044,435 A | 9/1991 | Sperl et al. |
| 5,083,610 A | 1/1992 | Sheehy |
| 5,100,553 A | 3/1992 | Nomura et al. |
| 5,163,510 A | 11/1992 | Sunde |
| 5,297,625 A | 3/1994 | Premuzic et al. |
| 5,332,559 A | 7/1994 | Brierley et al. |
| 5,340,376 A | 8/1994 | Cunningham |
| 5,350,684 A | 9/1994 | Nakatsugawa et al. |
| 5,360,064 A | 11/1994 | Jenneman et al. |
| 5,363,913 A | 11/1994 | Jenneman et al. |
| 5,424,195 A | 6/1995 | Volkwein |
| 5,431,717 A | 7/1995 | Kohr |
| 5,492,828 A | 2/1996 | Premuzic et al. |
| 5,500,123 A * | 3/1996 | Srivastava ..................... 210/603 |
| 5,516,971 A | 5/1996 | Hurley |
| 5,551,515 A | 9/1996 | Fodge et al. |
| 5,630,942 A | 5/1997 | Steiner |
| 5,670,345 A * | 9/1997 | Srivastava et al. .............. 435/75 |
| 5,695,641 A | 12/1997 | Cosulich et al. |
| 5,766,930 A * | 6/1998 | Kohr .......................... 435/262.5 |
| 5,858,766 A | 1/1999 | Premuzic et al. |
| 5,885,825 A | 3/1999 | Lin et al. |
| 5,919,696 A | 7/1999 | Ikeda et al. |
| 6,265,205 B1 | 7/2001 | Hitchens et al. |

(Continued)

FOREIGN PATENT DOCUMENTS

AU    2004229070 A1    6/2005

(Continued)

OTHER PUBLICATIONS

Shumkov et al. "Effect of enclosing rocks and aeration on methanogenesis from coals". Appl. Microbiol Biotechnol. 1999, 52: 99-103.*

(Continued)

Primary Examiner — Vera Afremova
(74) Attorney, Agent, or Firm — Dickstein Shapiro LLP

(57) ABSTRACT

A method of producing fuel from biodegradable carbonaceous material using a stacked particle bioreactor is provided. A stacked particle bioreactor is formed from particles including biodegradable carbonaceous material. The biodegradable carbonaceous material in the stacked particle bioreactor is aerobically and/or anaerobically bioconverted into one or more synfuels, which are collected from the reactor. The synfuels produced by the method may include synthetic petroleum, alcohol, and/or a gaseous fuel containing methane. Preferably the method includes an aerobic biotreatment phase followed by an anaerobic bioconversion phase. A stacked particle bioreactor for carrying out the anaerobic, and preferably aerobic, degradation is also described.

24 Claims, 4 Drawing Sheets

U.S. PATENT DOCUMENTS

| | | | |
|---|---|---|---|
| 6,342,378 B1 * | 1/2002 | Zhang et al. | 435/168 |
| 6,410,304 B2 | 6/2002 | Kohr | |
| 6,543,535 B2 | 4/2003 | Converse et al. | |
| 6,630,067 B2 * | 10/2003 | Shieh et al. | 210/139 |
| 6,652,622 B2 | 11/2003 | Kohr | |
| 6,797,508 B1 * | 9/2004 | Holker | 435/252.1 |
| 6,802,888 B2 * | 10/2004 | Kohr et al. | 75/712 |
| 2001/0001065 A1 | 5/2001 | Kohr | |
| 2005/0035058 A1 | 2/2005 | Forrestal et al. | |
| 2005/0112741 A1 | 5/2005 | Kohr | |
| 2008/0020437 A1 | 1/2008 | Savarese | |

FOREIGN PATENT DOCUMENTS

| | | |
|---|---|---|
| CA | 2 605 591 | 10/2006 |
| CL | 2580-98 | 10/1997 |
| DE | 31 02 739 A1 | 11/1982 |
| DE | 44 09 487 A1 | 4/1995 |
| DE | 196 28 521 A1 | 1/1998 |
| JP | 2003019491 * | 1/2003 |
| WO | WO 79/00201 | 4/1979 |
| WO | WO 95/05451 | 2/1995 |
| WO | WO 98/24730 | 6/1998 |
| WO | WO 2005/047452 A1 | 5/2005 |
| WO | WO 2005/113459 A1 | 12/2005 |
| WO | WO 2005/115930 A1 | 12/2005 |

OTHER PUBLICATIONS

Wadhwa et al. World Journal of Microbiology and Biotechnology. 1988, vol. 14, pp. 751-763.*

Anderson, R.T. and Lovley, D.R., "Hexadecane Decay by Methanogenesis," Nature, Apr. 13, 2000, 404:722.

Anderson et al., "Anaerobic Benzene Oxidation in the Fe(III) Reduction Zone of Petroleum-Contaminated Aquifers," Environ. Sci. Technol. vol. 32, No. 9: 1222-1229 (Mar. 18, 1998).

Belyaev, S.S. et al., "Methanogenic Bacteria for the Bondyuzhskoe Oil Field: General Characterization and Analysis of Stable-Carbon Isotopic Fractionation," Appl. And Environ. Microbiol. 45, No. 2:691-697 (Feb. 1983).

Bernard, F.P. et al., "Indigenous Microorganisms in Connate Water of Many Oil Fields: A New Tool in Exploration and Production Techniques," Society of Petroleum Engineers, SPE 24811, 467-476 (Oct. 4-7, 1992).

"Biological Gasification of Coals Final Report," U.S. Department of Commerce, National Technical Information Service, 40-63 (Mar. 1990).

Brown, L.R. et al., "Slowing Production Decline and Extending the Economic Life of an Oil Field: New MEOR Technology," SPE (Society of Petroleum Engineers) 59306, 1-16 (2000).

Coates, J.D. et al., "Anaerobic Hydrocarbon Degradation in Petroleum-Contaminated Harbor Sediments under Sulfate-Reducing and Artificially Imposed Iron-Reducing Conditions," Environ. Sci. Technol. 30: 2784-2789 (1996).

Connan, J. et al., "Anaerobic Biodegradation of Petroleum in Reservoirs: A Widespread Phenomenon in Nature," Abstract, 18th Int'l Meeting on Organic Geochemistry, Sep. 1997, Maastricht, The Netherlands.

Donaldson, E.C. and Clark, J. B., "Conference Focuses on Microbial Enhancement of Oil Recovery," Oil & Gas Journal, 47-52 (Dec. 20, 1982).

Grbić-Galić, D. et al., "Transformation of Toluene and Benzene by Mixed Methanogenic Cultures," Applied and Environmental Microbiology, 254-260 (Feb. 1987).

Groudeva, V.I. et al., "Enhanced oil Recovery by Stimulating the Activity of the Indigenous Microflora of Oil Reservoirs," Biohydrometallurgical Technologies, vol. 2, Torma, A.E. et al. (eds.), 349-356 (1993).

Gullapalli, I.L. et al., "Laboratory Design and Field Implementation of Microbial Profile Modification Process," SPE Reservoir Eval. & Eng. 3(1):42-49 (Feb. 2000).

Hales, B.A. et al., "Isolation and Identification of Methanogen-Specific DNA from Blanket Bog Peat by PCR Amplification and Sequence Analysis," Applied and Environmental Microbiology, vol. 62, No. 2: 668-675 (1996).

Hermann, M., "Anaerobic Microflora of Oil Reservoirs Microbiological Characterization of Samples From Some Production Wells, Bacterial Gas," pp. 223-234 (1992).

Hunkeler, D. et al., "Petroleum Hydrocarbon Mineralization in Anaerobic Laboratory Aquifer Columns," Journal of Contaminant Hydrology 32, 41-61 (1998).

Ivanov, M.A. et al., "Additional Oil Production During Field trials in Russia, Microbial Enhancement of Oil Recovery—Recent Advances," pp. 373-381 (1992).

Ivanov, M.A. et al., "Microbial Formation of Methane in an Oil Deposit Being Developed, Isotopes and their Uses in the Geosciences, in Mining Safety and in Environment Protection, Part II," published by Rector of the Freiberg Mining Academy (1982).

Le Blanc, L., "Artificial recharge," Offshore, p. 10 (Feb. 2000).

L'Haridon, S. et al., "Hot subterranean biosphere in a continental oil reservoir," Nature, vol. 377, pp. 223-224 (Sep. 21, 1995).

Magot, M. et al., "Microbiology of Petroleum Reservoirs," Antonie van Leeuwenhoek, 77:103-116 (2000).

McDonald, I.R. et al., "Molecular Ecological Analysis of Methanogens and Methanotrophs in Blanket Bog Peat," Microb. Ecol., 38(3):225-233 (Oct. 1999).

"Microbial Enhanced Oil Recovery," Developments in Petroleum Science, v.22 p. 9-12, 121-123, 149 (E.C. Donaldson et al. eds., 1989).

Mingzhai, L. et al., "Advances in Simulated Test of Biogas," Oil & Gas Geology, vol. 17, No. 2, pp. 117-122 (Jun. 1996) (in simplified Chinese with English abstract).

Nazina, T.N. et al., "Microbial Oil Transformation Process Accompanied by Methane and Hydrogen-Sulfide Formation," Geomicrobiology Journal, 4, No. 2:103-130 (1985).

Nazina, T.N. et al., "Occurrence and Geochemical Activity of Microorganisms in High Temperature, Water-Flooded Oil Fields of Kazakhstan and Western Siberia," Geomicrobiology Journal, 13:181-192 (1995).

Ng, T.K. et al., "Possible Nonanthropogenic Origin of Two Methanogenic Isolates from Oil-Producing Wells in the San Miguelito Field, Ventura County, California," Geomicrobiology Journal, 7:185-192 (1989).

Orphan, V.J. et al., "Culture-Dependent and Culture-Independent Characterization of Microbial Assemblages Associated with High-Temperature Petroleum Reservoirs," Applied and Environmental Microbiology, vol. 66, No. 2:700-711 (Feb. 2000).

Panow, A. et al., "Mechanisms of Biologically-Mediated Methane Evolution from Black Coal," Fuel Processing Tech. 52:115-125 (1997).

Parkes, J., "Cracking Anaerobic Bacteria," Nature, v. 401 (Sep. 16, 1999).

Revesz, K et al., "Methane Production and Consumption Monitored by Stable H and C Isotope Ratios at a Crude Oil Spill Site, Bemidji, Minnesota," Applied Geochemistry, 10:505-516 (1995).

Rooney-Varga, J.N. et al., "Microbial Communities Associated with Anaerobic Benzene Degradation in a Petroleum-Contaminated Aquifer," Applied and Environmental Microbiology, vol. 65, No. 7, pp. 3056-3063 (Jul. 1999).

Rozanova, E.P. et al., "Microbiological Processes in a High-Temperature Oil Field," Microbiology 70, No. 1:102-110 (2001).

Schink, B., "Energetics of Syntrophic Cooperation in Methanogenic Degradation," Microbiology and Molecular Biology Reviews, 61, No. 2:262-280 (Jun. 1997).

Volkwein, J.C. et al., "Biological Production of Methane from Bituminous Coal," Fuel Processing Tech. 40:339-345 (1994).

Weiner, J.M. and Lovely, D.R., "Rapid Benzene Degradation in Methanogenic Sediments from a Petroleum-Contaminated Aquifer," Appl. And Environ. Microbiol., vol. 64, No. 5:1937-1939 (May 1998).

Zengler, K. et al., "Methane Formation From Long-Chain Alkanes by Anaerobic Microorganisms," Nature, 401:266-269 (Sep. 16, 1999).

Zhang, R., "Biology and Engineering of Animal Wastewater Lagoons," University of California, Davis Biological and Agricultural Dept., pp. 1-9 (Jan. 18, 2001).

Zobell, C.E., "Bacterial Release of Oil from Sedimentary Materials," The Oil and Gas Journal, 62-65 (Aug. 2, 1947).

Wadhwa et al., "Microbial Pretrement of Coals: A tool for solubilization of lignite in Organic Solvent—Quinoline," World Journal of Microbiology & Biotechnology, 1988, vol. 14, pp. 751-763.

Shumkov et al., "Effect of Enclosing Rocks and Aeration on Methanogenesis from Coals," Appl. Microbiology and Biotechnology 1999, vol. 52, pp. 99-103.

Gibbons et al., "Intermediate-Scale, Semicontinuous Solid-Phase Fermentation Process for Production of Fuel Ethanol from Sweet Sorghum," Applied and Environmental Microbiology, Jan. 1986, pp. 115-122.

Gibbons et al., "Effects of Inoculum Size on Solid-Phase Fermentation of Fodder Beets for Fuel Ethanol Production," Applied and Environmental Microbiology, Oct. 1986, pp. 960-962.

Cabrera et al., "Ex-FERM Ethanol Production Using Chipped Sugarcane in Packed Bed Fermenters," European J. Appl. Microbiol Biotechnol, 1982, 14:21-28.

Gibbons et al., "Fuel Ethanol and High Protein Feed From Corn and Corn-Whey Mixture in a Farm-Scale Plant," Biotechnology and Bioengineering, 1983, 25:2127-2148.

Gibbons et al., A Continuous, Farm-Scale, Solid-Phase Fermentation Process for Fuel Ethanol and protein Feed Production from Fodder Beets, Biotechnology and Bioengineering, 1984, 26:1098:1107.

Rolz, "A New Technology to Ferment Sugarcane Directly: the Ex-FERM Process," Process Biochemistry, 1980, 15:2-6.

Rolz, "Ethanol from Sugar Crops," Enzyme Microb. Technol., 1981, 3:19-23.

Stampe et al., Energy Consumption of a Farm-Scale Ethanol Distillation System, Energy in Agriculture, 1983, 2:355-368.

Westby et al., "Farm-Scale Production of Fuel Ethanol and Wet Grain from Corn in a Batch Process," Biotechnology and Bioengineering, 1982, 24:1681-1699.

Bryan et al., "Solid-Phase Fermentation of Sweet Sorghum," for presentation at the 1982 winter meeting American Society of Agricultural Engineering, 18 pages. Dec. 1982.

Kargi et al., "Solid-State Fermentation of Sweet Sorghum to Ethanol in a Rotary-Drum Fementor," Biotechnology and Bioengineering, 1985, 27:1122-1125.

Kalogeris et al., "Design of a Solid-State Bioreactor for Thermophilic Microorganisms," Bioresource Technology, 1999, 67:313-315.

Hardin et al., "Approach to Designing Rotating Drum Bioreactors for Solid-State Fermentation on the Basis of Dimensionless Design Factors," Biotechnology and Bioengineering, 2000, 67:275-282.

Sato et al., "Pilot-Scale Solid-State Ethanol Fermentation by Inert Gas Circulation Using Moderately Thermophilic Yeast," J. Ferment. Technol., 1988, vol. 66, No. 2, 173-180.

M.O. Ngadi et al, "Solid State Ethanol Fermentation of Apple Pomace as Affected by Moisture and Bioreactor Mixing Speed", Journal of Food Science, vol. 57, No. 3, 1992.

K.D.. Kirby et al., "Production of Fuel Ethanol by Solid-Phase Fermentation" Biotechnology and Bioengineering. vol. XXII, pp. 2425-2427, 1980.

* cited by examiner

METHOD AND BIOREACTOR FOR PRODUCING SYNFUEL FROM CARBONACEOUS MATERIAL

FIELD

The present patent document relates to methods and bioreactors for biodegrading carbonaceous material into synfuel, including, for example, synthetic oil, alcohol, and/or gaseous fuel.

BACKGROUND

The value of methane as a potential fuel source has long been recognized and exploited. Because the current price of natural gas is about the same as petroleum in terms of BTUs, however, natural gas has evolved from a low-cost fuel source that was often a by-product of petroleum oil field production to a fuel source worth drilling for. The increasing value of natural gas has been driven by a number of factors, including the world's shrinking supply of petroleum reserves and the increasingly stricter environmental regulations placed on coal fired power plants. Generating electricity from coal, for example, releases twice the carbon dioxide as making it from natural gas. Burning coal also produces mercury vapor that has been estimated to contribute to over twenty percent of the world's mercury pollution. In addition, the burning of coal can release arsenic compounds and sulfur dioxide. As a result, expensive pollution control systems are now required for all new coal fired plants and most existing plants.

The demand for gases that contain methane, such as natural gas and synthetic natural gas, will likely continue to increase in the future, not only because of the increasing demand for cleaner burning fuels, but also because the world's demand for petroleum will continue to drive its price higher, particularly as known petroleum reserves are depleted. The demand for methane will also likely increase as hydrogen fuel cells are commercialized. This is because the least expensive process for producing hydrogen involves chemically converting methane and water to hydrogen and carbon dioxide in the presence of a catalyst.

To satisfy demand for natural gas, the U.S. currently imports about 2 billion cubic feet of liquid natural gas ("LNG") per day. Importing LNG has at least two significant draw backs. First, the cost of importing LNG is high. Second, it is risky to have large LNG terminals located in major seaports in the present world environment, as such terminals could be the subject of terrorist attack. Even in the absence of terrorism, however, such terminals pose a significant explosion risk.

Because of the world's increasing demand for methane gas and cleaner burning fuels in general, alternative sources of gaseous fuels that contain methane are needed. As a result, an economical technique for producing gaseous fuels that contain methane and/or a liquid synfuel, such as synthetic petroleum, would have significant market value.

Artificial gas for use as heating fuel and derived from coal or coke was widely used during the latter part of the nineteenth century and during the first few decades of the twentieth century in the U.S. Because of the great availability and, at one time, apparent inexhaustible supply of natural gas in the U.S., as well as a few other areas in the world, manufactured gases were phased out rapidly. The use of natural gas, on the other hand, increased 730% between 1940 and 1970 in the U.S. During this period, the U.S. gas industry produced 313 trillion cubic feet of natural gas. However, in other parts of the world where natural gas was in short supply locally, manufactured gas has persisted.

Historically, the gasification of coal has involved the heating of coal through pyrolysis, carbonization, or retorting to cause its decomposition and gasification. The gas resulting from the gasification process typically contains varying concentrations of carbon monoxide, carbon dioxide, methane, and hydrogen, the concentration of each constituent depending on the particular gasification technique employed. Thus, while gasification is the key step in these heat based gasification techniques, it must be appreciated that it is only one step of the overall process of forming a manufactured or synthetic natural gas ("SNG") from coal. In addition to the gasification step, such processes typically include gas conditioning, gas purification, methanation and by-product treatment processes. Further, purification of the product gas from the coal gasification step to a degree of purity required for methane synthesis is difficult due to the large quantities and variety of impurities in the gas.

Another draw back of coal gasification using known heat gasification techniques is that the gasification process is a highly endothermic process, and the heat requirements of the process have to be covered by the addition of heat. This may be accomplished through, for example, direct heat supplied through the partial combustion of the coal with oxygen or indirect heat supplied from an external fuel source. In either event, however, a significant portion of the overall energy values contained in the coal prior to gasification are expended to gasify the coal. Finally, the heat based gasification processes do not appear to have any applicability to animal or plant waste, both significant renewable resources of carbonaceous materials.

The biological conversion of organic matter into methane has also been studied for many years. The degradation of organic matter to methane and carbon dioxide (i.e., methanogenic degradation) occurs in limited oxygen or other electron acceptor environments. This process is widespread in swamps, rice paddies, peat bogs, and in the intestinal tract of ruminant animals and plays a major role in the global carbon cycle. Indeed, the total biological methanogenic production of methane is estimated at 500 million tonnes per year, making methane the second most abundant greenhouse gas.

Methanogenic degradation is slower and less exergonic than aerobic degradation. However, aerobic degradation does not produce methane. More importantly, methanogenic conversion only releases about 15% of the energy that is released by complete aerobic conversion of the same organic carbon compound to carbon dioxide and water. This is because the remaining 85% of the energy is stored in the resulting methane for subsequent oxidation.

Methanogens are a group of Archaea that produce methane in anaerobic or anoxic environments. They are obligate anaerobes, and thus cannot tolerate any molecular or ionic oxygen in their environment. They form an interdependent relationship with other organisms, including bacteria, protozoa, insects, and grass feeding animals, such as cows. They use simple organic compounds (e.g., formate, acetate, methylamines and several alcohols) produced by those organisms and carbon dioxide as an energy source to produce methane.

Although methanogens depend on fermentative organisms to produce the simple organic substrates on which they rely for energy, fermentative microorganisms likewise depend on methanogens to remove hydrogen and the simple organic compounds they produce to improve their energetics. This interdependence is called syntrophic cooperation. In this cooperative relationship, the fermentative microorganism species ferment long chain organic carbon molecules to $H_2$ and C-1 and C-2 compounds for the methanogens to feed upon. This fermentation process is inhibited by the $H_2$ and C-1 and C-2 compounds produced. Methanogens, however, oblige these fermenting species by removing the hydrogen and C-1 and C-2 compounds as they convert them to methane. As a result, the syntrophically cooperating anaerobes cooperate in the conversion of complex organic matter to methane and carbon dioxide with very little loss of the energy values contained in the original organic matter. Recent advances in molecular biology have led to a better understanding of this complex, but widespread natural process.

A more in depth review of methanogenic degradation and a list of some methanogenic microorganisms is provided in B. Schink, *Energetics of Syntrophic Cooperation in Methanogenic Degradation*, Microbiology and Molecular Biology Reviews, 61:262-280 (June 1997), which is hereby incorporated by reference.

Long before the biology of methanogenic degradation was understood, people attempted to exploit methanogenic degradation to produce methane for its fuel value. For example, U.S. Pat. No. 1,990,523, which issued to Buswell et al. in 1935, describes a method for methane generation using anaerobic bacteria conversion of sewage.

Much effort has also been devoted to developing in situ microbial processes for the conversion of low-grade fossil fuels to methane. For example, U.S. Pat. No. 3,826,308, which issued to Compere-Whitney in 1974, and U.S. Pat. No. 5,424,195, which issued to Volkwein in 1995, focused on treating very low-grade coal that was left behind in underground mines. In U.S. Pat. No. 6,543,535, which issued to Converse et al. in 2003, a process for the in situ bioconversion of hydrocarbons to methane in hydrocarbon-bearing formations is described. The process described in the Converse et al. patent includes altering the environment of the hydrocarbon bearing formations so as to stimulate the growth of native microbes found within the formations.

Some of the subterranean microbial hydrocarbon conversion processes described in the literature have also used explosives in an effort to increase the surface area of coal or oil shale deposits being microbially treated. The explosions create what is called a "rubble chimney." While formation of a rubble chimney increases the rate of conversion to methane, the overall conversion rate remains relatively slow.

Biological processes have also been used to aid in the recovery of petroleum from oil reserves. For example, U.S. Pat. No. 2,413,278, which issued to Zobell in 1946, U.S. Pat. No. 2,807,570, which issued to Updegraff in 1957, and U.S. Pat. No. 2,907,389, which issued to Hitzman in 1959, teach ways to use bacteria to generate extra recovery of petroleum from oil reservoirs after 40 to 50% of the contained oil has been removed by pumping and water flooding. The process of using bacteria to recover additional oil from underground reservoirs is called Microbial Enhanced Oil Recovery (MEOR).

One of the major limitations of in situ microbial gasification and MEOR processes is not the general ability of the bacteria used in those processes to dislodge oil, reduce viscosity or convert oil to methane, but rather the problems encountered with providing the right environment for microbial growth in the deep underground reservoirs or formations. Within such environments a variety of environmental factors may be encountered that individually or collectively inhibit to varying degrees, or even prevent, the microbial conversion or degradation process. Such environmental challenges can include, for example, high temperatures, high concentrations of salts or other biocides, and limited porosity of the native rock in which the oil is being held, as this will restrict the accessibility of microbes to the oil. And though it may be possible to modify the environment of a formation to some degree, sometimes it will not be possible or practical to alter the environment of a formation sufficiently to have a practical impact on microbial activity.

A need exists, therefore, for an ex situ process that is capable of converting vast quantities of low-grade fossil fuels, as well as other organic carbonaceous materials, into one or more synfuels, including methane and/or oil. While biodegradation of low-grade fossil fuels can theoretically be performed in stirred tank bioreactors, due to the relatively long residence time that will be necessary to convert such carbonaceous materials to oil and/or a gaseous fuel and the large amount of material that will need to be processed to yield relatively small quantities of fuel values, the cost of scaling a stirred tank processes up to commercial scale is simply too high to make stirred tank bioreactors a practical option. On the other hand, a very large, low-cost, yet relatively efficient, heap bioreactor could economically unlock the trillions of barrels of oil in the world's resources of oil shale and oil sands. Such a bioreactor could also be used in the biogasification of other organic carbonaceous materials, including renewable resources such as plant and animal wastes, as well as other non-renewable resources such as coal. The synfuel (e.g., methane, alcohol, and/or synthetic petroleum oil) produced in such bioreactors could help fuel an energy-hungry world for the rest of the century.

In view of the foregoing, one object of the present invention is to provide a new bioreactor design for use in converting organic carbonaceous materials into synfuel. Another, and separate, object is to provide a new method for converting organic carbonaceous materials into synfuel.

SUMMARY

The present patent document is directed to methods and bioreactors for bioconverting organic carbonaceous material into synfuel. The resulting synfuel may be, for example, synthetic petroleum, alcohol, and/or a gaseous fuel containing methane.

According to one embodiment, a stacked particle bioreactor is formed from particles comprising biodegradable carbonaceous material. The stacked particle bioreactor is then biotreated to convert carbonaceous material within the bioreactor into synfuel, which is then collected from the bioreactor. The synfuel is preferably synthetic petroleum, alcohol, and/or a gaseous fuel.

The size and size distribution of the particles used to form the bioreactor are preferably chosen so that a large percent of the carbonaceous material is exposed to the microbes used to perform the biotreatment. The void volume of the reactor is preferably greater than or equal to about 15%, and more preferably greater than or equal to about 20%. A preferred range for the void volume of the reactor is between about 15% and 35%, and more preferably between about 20% and 35%. Preferably the void volume is substantially uniform throughout the reactor.

The biodegradable carbonaceous material treated in the bioreactor may include, for example, oil sands, carbonaceous rock, asphalt, asphaltic oil, waste oil, bitumen, tar, pitch, kerogen, rubber, and agricultural waste.

One or more cultures may be used to biotreat the stacked particle bioreactor, with each culture comprising a single type of microorganism or a group of different microorganisms. Typically, the cultures will comprise a group of different microorganisms. Further, the microorganisms used to biotreat the carbonaceous material in the reactor may be aerobic, facultative anaerobic, or anaerobic microorganisms. In a particularly preferred embodiment, the biotreatment begins as an aerobic microbial degradation process and then is converted to an anaerobic microbial degradation process. In other implementations, however, it may be desirable to perform only an aerobic biotreatment or only an anaerobic biotreatment.

If the carbonaceous material within the bioreactor is to be anaerobically biotreated, the bioreactor should be designed so that new cultures of microbes can be introduced anaerobically into the bioreactor and dispersed efficiently throughout the bioreactor.

Each of the microorganisms used to perform the biodegradation will typically perform one of the following biochemical processes during the biotreatment: 1) produce surface-tension reducing compounds or solvents that release native petroleum from the carbonaceous material, 2) ferment the carbonaceous material into smaller organic compounds, including, for example, synthetic petroleum, alcohol and/or simple organic compounds, or 3) convert simple organic compounds resulting from the fermentation process into a biogas comprising methane. Thus, whether synthetic petroleum, alcohol, a gaseous fuel, or all three are collected from the stacked particle bioreactor will depend on the feedstock, the types of microorganisms used to perform the biotreatment, and the extent to which the digestion of the carbonaceous material within the bioreactor is carried out.

For example, while the principal end products of aerobic degradation of organic carbon compounds are carbon dioxide and water, in reaching the final aerobic degradation products, aerobic and facultative anaerobic microorganisms perform the first and second biochemical processes identified above. Thus, by stopping the aerobic degradation reactions before completion is reached synthetic petroleum or alcohol may be produced from a wide variety of carbonaceous materials. Further, if desired, all of, or some portion of, the organic compounds produced during the aerobic fermentation phase may be further digested and converted to methane during a subsequent anaerobic biotreatment. As such, the aerobic fermentation products within the bioreactor are considered to be part of the biodegradable carbonaceous material in the bioreactor for purposes of the present patent document.

The principal end products of anaerobic degradation of organic carbon compounds are methane and carbon dioxide. In reaching those final degradation products, however, fermentative anaerobes and facultative anaerobes will perform the first and second biochemical processes identified above, while methanogens will perform the third. Thus, it is possible to collect synthetic petroleum products and alcohol from the bioreactor as larger molecular weight carbon compounds are anaerobically degraded, particularly large molecular weight hydrocarbons. If, however, anaerobic degradation is permitted to go to completion on at least some of the organic carbonaceous material in the bioreactor, a biogas comprising methane will be produced.

After formation, the stacked particle bioreactor will continue to produce synfuel for a period of several months or years. The liquid and/or gaseous synfuel produced in the bioreactor may be collected and removed from the bioreactor by a network of pipes incorporated into the bioreactor during its construction.

According to another embodiment, a method of producing gaseous fuel from carbonaceous material using a stacked particle bioreactor is provided. The method comprises the steps of a.) forming a stacked particle bioreactor from particles that include biodegradable carbonaceous material; b.) forming an anaerobic microorganism supporting environment within the bioreactor; c.) anaerobically bioconverting biodegradable carbonaceous material in the stacked particle bioreactor into a gaseous fuel; and d.) collecting the gaseous fuel from the bioreactor. Preferably the gaseous fuel produced and collected in the method comprises methane.

In a particularly preferred implementation of the embodiment, the stacked particle bioreactor is aerobically biotreated prior to forming an anaerobic environment within the bioreactor. This is done to aerobically ferment carbonaceous material in the bioreactor and/or release native oil from the carbonaceous material. Preferably, the method also includes the step of collecting oil from the stacked particle bioreactor.

The anaerobic environment within the bioreactor may be formed, for example, by covering the stacked particle bioreactor with a gas impermeable barrier, such as a clay or plastic barrier layer. Although the reactor will naturally turn anaerobic with such a barrier over time unless air or oxygen are introduced into the covered bioreactor, the bioreactor may also be purged with argon, nitrogen, carbon dioxide, ammonia or hydrogen gas to speed up the conversion of its environment to an anaerobic microorganism supporting environment. In addition to purging oxygen from the reactor, these gases may provide necessary nutrients for the microorganisms in the bioreactor or precursors for methane production (e.g., carbon dioxide and hydrogen).

If the biodegradable carbonaceous material includes particles less than about 0.3 cm, it may be desirable to agglomerate the particles prior to forming the stacked particle bioreactor. Preferably, the resulting agglomerates have a particle size in the range of about 0.3 cm to about 2.54 cm. Alternatively, the particles of biodegradable carbonaceous material may be coated on the surface of a plurality of substrates having a particle size greater than or equal to about 0.3 cm and preferably less than or equal to about 5 cm, and more preferably less than or equal to about 2.54 cm. The coating technique is particularly advantageous when the substrates are significantly larger than the particles of biodegradable carbonaceous material to be coated thereon. For the particles of carbonaceous material to properly coat on the substrates, typically they should have a particle size of about 250 µm or less.

According to yet another embodiment, the particles are screened into two or more size fractions and then a plurality of stacked particle bioreactors having a void volume greater than or equal to about 15% are formed, with each bioreactor being formed from the particles from one of the separated size fractions. Preferably if one of the size fractions includes a significant fines fraction, or substantial number of particles less than about 0.3 cm in diameter, that size fraction is preferably agglomerated to form particulates having a particle size in the range of 0.3 cm to 2.54 cm before forming a bioreactor with that size fraction.

According to yet another embodiment, a method of converting biodegradable carbonaceous material into synfuel using a stacked particle bioreactor is provided. According to the method, a stacked particle bioreactor is formed from particles comprising biodegradable carbonaceous material. The bioreactor is inoculated with a culture comprising one or more aerobic and/or facultative anaerobic microorganisms capable of fermenting carbonaceous matter. The carbonaceous matter in the stack is aerobically fermented, and synthetic petroleum and/or gaseous fuel is collected from the stack. The environment within the stack is converted from an aerobic environment to an anaerobic environment, and the stack is inoculated with a culture comprising one or more anaerobic microorganisms. The aerobically biotreated stack is then anaerobically biotreated to produce synthetic petroleum and/or gaseous fuel. Finally, synthetic petroleum and/or gaseous fuel is collected from the anaerobically biotreated stack.

According to yet another embodiment, a method of bioconverting organic carbonaceous material into synfuel using a stacked particle bioreactor is provided. The method according to the present embodiment comprises the steps of: a.) coating the surface of a plurality of substrates having a particle size greater than or equal to about 0.3 cm with organic carbonaceous material and thereby forming a plurality of coated substrates; b.) forming a stacked particle bioreactor with the coated substrates, the stacked particle bioreactor having a void volume greater than or equal to about 15%; c.) forming an anaerobic environment within the stacked particle bioreactor; d.) anaerobically biotreating the stacked particle bioreactor until a desired amount of organic carbonaceous material within the stacked particle bioreactor has been converted to a gaseous fuel; and e.) collecting the gaseous fuel from the stacked particle bioreactor.

Preferably the gaseous fuel produced and collected in the method comprises methane. Further, in a preferred implementation of the embodiment, synthetic petroleum is also collected from the stacked particle bioreactor.

The plurality of substrates may comprise, for example, one or more materials selected from the group consisting of oil shale, coal, rock, asphalt, rubber, and plant waste. Moreover, the types of plant waste that may be used as substrates in the method include, for example, plant waste selected from the group consisting of bark, corn cobs, nut shells, wood by-products, and crop by-products.

The organic carbonaceous material coated on the substrates may comprise, for example, an organic carbonaceous material selected from the group consisting of oil sands, oil shale, asphaltic oil, waste oil, bitumen, tar, pitch, kerogen, coal and agricultural waste. Further, the types of agricultural waste that may be coated on the substrates include, for example, manure, fruit waste, straw, fermentation waste, and pulverized plant waste. Grape skins are a particularly preferred form of fruit waste that may be coated on coarse substrates for biotreatment. In addition, rice straw is a particularly preferred form of straw that may be coated on the substrates for biotreatment.

Notably, the energy content of one pound of rice straw is about 6,500 Btu, which is similar to the energy content of some of the lignite coals. In the Sacramento Valley alone, approximately 1,500,000 tonnes of rice straw are produced annually. Thus, the energy content stored in the annual crop of rice straw from the Sacramento Valley is about $1.95 \times 10^{12}$ BTU, making it a potentially valuable renewable resource for producing synfuel.

As used herein, the term "coal" includes all types of coals, including, in order of decreasing metamorphic rank, anthracite coal, semianthracite coal, semibituminous coal, bituminous coal, subbituminous coal, lignite coal, peat coal, peat, and cannel coal. If coal is used as the organic carbonaceous material coated on the substrate, preferably the coal has a metamorphic rank of bituminous coal or less, and more preferably a metamorphic rank of peat or less. Moreover, if the organic carbonaceous material coated on the substrate comprises coal or oil shale, preferably the coating is a concentrate of these materials.

In a particularly preferred implementation of the present embodiment, the method further comprises the step of covering the stacked particle bioreactor with a gas impermeable barrier. The gas impermeable barrier may, for example, comprise a clay barrier layer or a plastic barrier layer.

The stacked particle bioreactor is also preferably inoculated with a culture comprising one or more aerobic and/or facultative anaerobic microorganisms. The organic carbonaceous material in the bioreactor is then aerobically fermented prior to an anaerobic environment being formed within the bioreactor. Preferably, the bioreactor is aerated during at least a portion of the aerobic fermentation.

An anaerobic environment may be formed within the bioreactor by reducing the oxygen concentration within the bioreactor through aerobic fermentation. Alternatively, or in addition, the stacked particle bioreactor may be purged with argon, nitrogen, carbon dioxide, ammonia or hydrogen gas.

According to a further embodiment, a method of bioconverting organic carbonaceous material into synfuel is provided comprising the steps of: a.) agglomerating particles comprising organic carbonaceous material with an agglomeration aid into a plurality of agglomerates having a particle size greater than or equal to about 0.3 cm; b.) forming a stacked particle bioreactor with the agglomerates, the stacked particle bioreactor having a void volume greater than or equal to about 15%; c.) forming an anaerobic environment within the stacked particle bioreactor; d.) anaerobically biotreating the stacked particle bioreactor until a desired amount of organic carbonaceous material within the stacked particle bioreactor has been converted to a gaseous fuel; and e.) collecting the gaseous fuel from the stacked particle bioreactor. Preferably the gaseous fuel comprises methane as in the other embodiments. In addition, synthetic petroleum is preferably collected from the stacked particle bioreactor as it drains from the bioreactor.

The particles used to form the agglomerates may comprise a wide variety of organic carbonaceous materials, including one or more selected from the group consisting of oil sands, carbonaceous rock, asphalt, rubber, and agricultural waste. Suitable agricultural wastes include, for example, bark, corn cobs, nut shells, wood by-products, and crop by-products. Suitable carbonaceous rocks include any of the coals and oil shale. Coal particles used to form the agglomerates preferably have a metamorphic rank of bituminous coal or less, and more preferably a metamorphic rank of peat or less.

The method also preferably includes the step of covering the stacked particle bioreactor with a gas impermeable barrier. The gas impermeable barrier may, for example, comprise a clay barrier layer or a plastic barrier.

The stacked particle bioreactor is also preferably inoculated with a culture comprising one or more aerobic and/or facultative anaerobic microorganisms. The organic carbonaceous material in the bioreactor is then aerobically fermented prior to an anaerobic environment being formed within the bioreactor. Preferably, the bioreactor is aerated during at least a portion of the aerobic fermentation.

An anaerobic environment may be formed within the bioreactor by reducing the oxygen concentration within the bioreactor through aerobic fermentation. Alternatively, or in addition, the stacked particle bioreactor may be purged with argon, nitrogen, carbon dioxide, ammonia or hydrogen gas.

The plurality of agglomerates may also be coated with a liquid or semi-liquid carbonaceous material such as asphaltic oil, waste oil, bitumen, tar, pitch, and kerogen to increase the concentration of carbonaceous material within the bioreactor and to provide a readily biodegradable source of organic compounds for the microorganisms to biodegrade within the bioreactor.

According to a further embodiment, a method of converting organic carbonaceous material into synfuel is provided comprising the steps of: a.) providing particles of solid carbonaceous organic material having a particle size of less than about 5.0 cm; b.) screening the particles into two or more size fractions; c.) forming a plurality of stacked particle bioreactors having a void volume greater than or equal to about 15%, each bioreactor being formed with particles from one of the separated size fractions; d.) forming an anaerobic environment within each of the stacked particle bioreactors; e.) anaerobically biotreating each of the stacked particle bioreactors until a desired amount of organic carbonaceous material within the stacked particle bioreactor has been converted to a gaseous fuel; and f.) collecting gaseous fuel from each of the stacked particle bioreactors. Preferably the gaseous fuel comprises methane as in the other embodiments. In addition, synthetic petroleum is preferably collected from the stacked particle bioreactor.

The particles of solid organic carbonaceous material may comprise a wide range of solid organic carbonaceous materials, including, for example, oil sands, carbonaceous rock, asphalt, rubber, and agricultural waste. Suitable agricultural waste for use in the method, includes, for example, one or more plant wastes selected from the group consisting of bark, corn cobs, nut shells, wood by-products, and crop by-products. Suitable carbonaceous rocks for use in the method include any of the coals and oil shale.

Preferably the method further includes the step of covering each of the stacked particle bioreactors with a gas impermeable barrier. The stacked particle bioreactor is also preferably inoculated with a culture comprising one or more aerobic and/or facultative anaerobic microorganisms. The organic carbonaceous material in the bioreactor is then aerobically fermented prior to an anaerobic environment being formed within the bioreactor. Preferably, the bioreactor is aerated during at least a portion of the aerobic fermentation.

Preferably a liquid or semi-liquid carbonaceous material such as asphaltic oil, waste oil, bitumen, tar, pitch, and kerogen is added to at least one of the bioreactors to increase the concentration of carbonaceous material within the bioreactor and to provide a readily biodegradable source of organic compounds for the microorganisms to biodegrade within the bioreactor.

According to another aspect of the invention, a bioreactor for converting biodegradable carbonaceous material into synfuel is provided. According to one embodiment, the bioreactor comprises a.) a plurality of particles stacked to form a heap having a void volume of greater than or equal to about 15%, the particles comprising biodegradable carbonaceous material; b.) means for communicating gases to the heap; c.) means for communicating aqueous solutions to the heap; d.) means for communicating gas from the heap; e.) means for collecting liquids that drain from the heap; f.) a gas impermeable barrier covering the heap; and g.) a microbial consortium within the heap capable of biodegrading biodegradable carbonaceous material within the heap to synfuel.

Further aspects, objects, desirable features, and advantages of the invention will be better understood from the detailed description and drawings that follow in which various embodiments of the disclosed invention are illustrated by way of example. It is to be expressly understood, however, that the drawings are for the purpose of illustration only and are not intended as a definition of the limits of the invention.

DETAILED DESCRIPTION OF THE PREFERRED EMBODIMENTS

Consistent with its ordinary meaning, the term "synfuel" is used herein to refer to a liquid or gaseous fuel derived from a fossil fuel that is solid, such as coal, or part of a solid, such as tar sands or oil shale, or from fermentation. The synfuel produced may be, for example, synthetic petroleum, alcohol, and/or a gaseous fuel containing methane.

As used herein, the terms "biodegradable carbonaceous material" and "organic carbonaceous material" are essentially interchangeable and refer to carbonaceous feedstock which can be used in the processes or bioreactors of the present invention to produce synfuel. It should be appreciated that those terms are also intended to encompass and refer to organic fermentation products derived from the original carbonaceous feedstock that are within the bioreactor.

Figure 1:
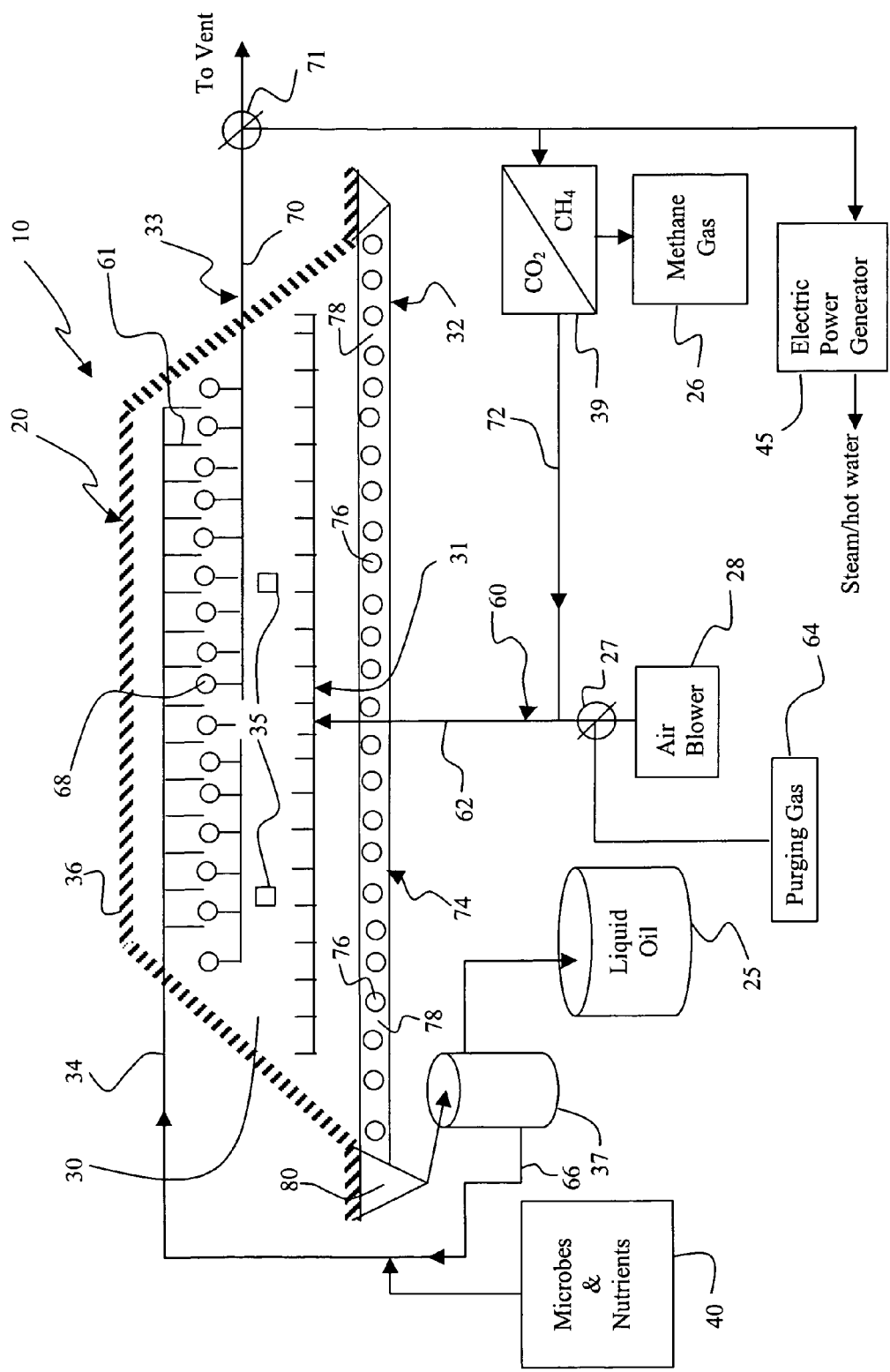
FIG. 1 schematically illustrates a biodegradation power plant and its corresponding bioreactor and associated equipment for recovering synfuel from carbonaceous material.

FIG. 1 schematically illustrates a biodegradation power plant 10. Power plant 10 includes a stacked particle bioreactor 20. In the present embodiment, bioreactor 20 includes a heap 30 comprised of a plurality of stacked particles and a gas impermeable barrier 36 covering heap 30. Barrier 36 is provided so that bioreactor 20 may be operated in an anaerobic mode. If bioreactor 36 will not be operated in an anaerobic mode then barrier 36 is unnecessary.

Stacked particle bioreactor 20 may be formed by stacking particles comprising biodegradable carbonaceous material so as to form a heap 30. The stacked particle bioreactor 20 is then aerobically and/or anaerobically biotreated to convert carbonaceous material within the bioreactor 20 into synfuel, which is then collected from the bioreactor, for example, by way of liquid collection system 32 and/or gas collection system 33.

The biodegradable carbonaceous material treated in the bioreactor 20 may include, for example, oil sands, carbonaceous rock, asphalt, asphaltic oil, waste oil, bitumen, tar, pitch, kerogen, rubber, and agricultural waste. Carbonaceous rock materials that may be processed in the methods and bioreactors of the present invention include, for example, all of the different coals and oil shale. Lower rank coals are particularly preferred due to the fact that they have less fixed carbon, have higher hydrogen concentrations, and are generally easier to biodegrade. Thus, it is preferred that the coal have a metamorphic rank of bituminous coal or below, more preferably of lignite coal or below, and even more preferably of peat or below.

Both natural and synthetic asphalt may be processed in the methods and bioreactors of the present invention, thus providing a new use and alternative means of disposing of asphalt stripped from road surfaces. Similarly, shredded or ground tires may be used as a source of rubber in the methods and bioreactors of the present invention. Agricultural waste includes both animal and plant waste, useful examples of which include manure, bark, corn cobs, nut shells, wood by-products, crop by-products, fruit waste, straw, fermentation waste, and pulverized plant waste.

A large variety of stacked particle bioreactors designs may be employed to practice the methods of the present invention. In fact, many of the heap bioreactor designs used in heap bioleaching of metal ores may be adapted for use in the present invention. Further, the size and size distribution of the particles used to form the bioreactor 20 are preferably chosen so that a large percent of the carbonaceous material is exposed to the microbes used to perform the biotreatment. The size and size distribution of the particles are also preferably selected so that the void volume of the reactor 20 is greater than or equal to about 15% and more preferably greater than or equal to about 20%. A preferred range for the void volume for the reactor 20 is between about 15% and 35%, and more preferably between about 20% and 35%. It is also desirable for the void volume to be substantially uniform throughout the reactor.

For bioreactors 20 that are aerobically biotreated, generally void volumes on the higher side of the above ranges will be desired, as good permeability will be needed for oxygen and liquid transfer within the heap. Although, the same level of permeability is not required for bioreactors that are to be exclusively or primarily anaerobically biotreated, permeability in such bioreactors remains important. This is because permeability is still required in such reactors for pH and temperature control, precise low level oxygen control, and efficient changeover to aerobic conditions within the heap. Permeability is also needed to permit adequate liquid transfer within the heap so that inoculum and nutrients can reach all areas of the reactor. Further, one tonne of coal is capable of producing as much as 0.5 tonnes of methane gas. That is about a one thousand fold volume expansion. Thus, it is important that the reactor have adequate permeability so as to permit this gaseous synfuel to vent.

One or more cultures may be used to biotreat the stacked particle bioreactor 20, with each culture comprising a single type of microorganism or a group of different microorganisms. Typically, the cultures will comprise a group of different microorganisms. Further, the microorganisms used to biotreat the carbonaceous material in the reactor 20 may be aerobic, facultative anaerobic, or anaerobic microorganisms, and this may change over time. For example, in a particularly preferred embodiment, the biotreatment begins as an aerobic microbial degradation process and then is converted to an anaerobic microbial degradation process. In other implementations, however, it may be desirable to perform only an aerobic biotreatment or only an anaerobic biotreatment.

If an aerobic biotreatment is to be performed, then the heap 30 is preferably inoculated while heap 30 is being formed, or soon thereafter, with a microbial consortium that is capable of biodegrading the biodegradable carbonaceous material that will be processed in bioreactor 20. For example, inoculant may be sprayed onto the particles as they are being stacked, preferably conveyor stacked, to form the heap 30. Alternatively, each layer of particles laid down to form the heap 30 may be sprayed with inoculant prior to laying down another layer of particles. Further, if the agglomerates or coated particles discussed below are used to form the heap 30, then inoculation may also occur during the particle formation process. The foregoing inoculation techniques are not exclusive, and those skilled in the art will appreciate from the instant disclosure that there are a wide variety of other ways to inoculate bioreactor 20, including using the wild microorganism strains that are already present on the particles used to form the reactor.

If the carbonaceous material within the bioreactor 20 is to be anaerobically biotreated, then bioreactor 20 is preferably designed so that new cultures of microbes can be introduced anaerobically into the bioreactor and dispersed efficiently throughout the bioreactor. This may, for example, be accomplished through an irrigation system 34, which is in communication with a supply 40 of microbes and nutrients and water 66 recovered from oil/water separator 37. In the present embodiment, irrigation system 34 is preferably a drip irrigation system so as to permit gas impermeable barrier 36 to be positioned as closely as possible over heap 30. Irrigation system 34 is preferably positioned adjacent to the top portion of heap 30, so that all of heap 30 may be irrigated. However, it may also be desirable to have emitters 61 buried at various depths throughout the heap, with different portions of the irrigation system being independently controllable to enhance process control within the bioreactor 20.

The bacteria listed in Table 1 below may be used to aerobically biodegrade hydrocarbon materials found in fossil fuels such as coal, oil shale, and oil sand. In addition, wild strains found associated with these natural resources may also be used. The typical microorganisms found in a compost pile may be used to aerobically biodegrade the agricultural and organic waste in the bioreactor 20. Inoculum derived from aerobic or facultative lagoons may also be used.

TABLE 1

Aerobic and Facultative Anaerobic Organisms Capable of Degrading Long-chain Hydrocarbons

| | |
|---|---|
| Achromobacter paraffinoclastus | Micrococcus glutmicus |
| Acinetobacter calcoaceticus | Mycobacterium parafficum |
| Arthrobacter paraffineus | Micrococcus paraffinolyticus |
| Arthrobacter simplex | Mycobacterium smegmatis |
| Candida lipolyticum | Nocardia petrooleophila |
| Caphalosporium rosem | P. aeruginosa |
| Corynebacterium glutamicum | Pseudomonas fluorescens |
| Corynebacterium hydrocarboclastus | Torulopsis colliculosa |
| Corynebacterium petrophilum | Streptomyces argenteolus |
| Flavobacterium species | Streptomyces aureus |

The facultative microorganisms in Table 1 and the microorganisms listed in Table 3 below may be used to anaerobically ferment various carbonaceous materials within bioreactor 20. Further, the methanogenic microorganisms listed in Table 2 may be used to finish the biodegradation of the carbonaceous materials included in bioreactor 20 by converting the simple organic compounds resulting from aerobic and/or anaerobic fermentation into methane. Anaerobic microorganisms useful in the biodegradation of agricultural and other organic waste may also be readily obtained from, for example, cow manure or the sludge of facultative or anaerobic waste treatment ponds.

The bacteria and Archaea listed in Tables 1, 2, and 3 are all available from the American Type Culture Collection or like culture collections.

TABLE 2

Methanogenic Organisms

| | |
|---|---|
| Methanobacterium formicicum | Methanogenium cariaci |
| Methanobacterium thermautotrophicum | Methanogenium marisnigri |
| Methanobacterium wolfei | Methanogenium thermophilicum |
| Methanobacterium alcaliphilum | Methanogenium olentangyi |
| Methanobacterium thermoformicium | Methanogenium tationis |
| Methanobacterium thermalcaliphilum | Methanococcus vannielii |
| Methanobacillus omelianskii | Methanococcus voltae |
| Clostridium butyricum | Methanococcus maripaludis |
| Pelobacter acetylenicus | Methanococcus |
| Methanospirillum hungatei | thermolithotrophicus |
| Methanobrevibacter ruminantium | Methanomicrobium mobile |
| Methanobrevibacter smithii | Methanomicrobium payrnteri |

TABLE 2-continued

Methanogenic Organisms

| | |
|---|---|
| *Methanobrevibacter arboriphilicus* | *Methanococcoides methylutens* |
| *Methanothermus fervidus* | *Methanoplanus limicola* |
| *Methanothermus sociabilis* | *Methanolobus tindarius* |
| *Methanosphaera stadtmanae* | *Methanolobus siciliae* |
| *Methanosarcina barkeri* | *Methanolobus vulcani* |
| *Methanosarcina mazei* | *Methanothrix soehngenii* |
| *Methanosarcina thermophila* | *Methanothrix concilii* |
| | *Methanothrix thermoacetophila* |

TABLE 3

Anaerobic fermenting Microorganisms

| Organic Substrate | Digesting Anaerobe |
|---|---|
| Alcohol oxidation | *Desulfovibrio vulgaris, Thermoanaerobium brockii, Pelobacter venetianus,* and *Pelobacter carbinolicus.* |
| Oxidation of propionate | *Syntrophobacter wolinii, Syntrophobacter pfennigii* |
| Oxidation of butyrate | *Syntrophomonas wolfei, Syntrophomonas sapovorans, Syntrophospora bryantii* |
| Oxidation of acetate | *Clostridium ultunense* |
| Oxidation of glycolate | *Syntrophobotulus glycolicus* |
| Oxidation of aromatic compounds | *Syntrophus buswellii, Syntrophus gentianae* |

Whether one or more of the microorganisms listed in Tables 1-3 or wild strains are selected for use in the present process will depend on factors such as the type of carbonaceous material being biodegraded, the expected pH of the environment, and the expected temperatures in the heap during biodegradation. These selection criteria, however, are well within the skill of those in the art and need not be described in detail here. In general terms, however, it will be preferable to use a consortium of microorganisms during both aerobic and anaerobic biotreatments. Consortia of microorganisms are preferred because the environmental conditions (e.g., pH, temperature, Eh, nutrient types and concentrations, organic substrates, toxin levels, etc.) will typically vary throughout the heap 30. Thus, when a consortium is employed, the conditions within heap 30 will naturally select for those microorganisms that are best suited for the conditions that exist within heap 30, or some portion of it.

Moreover, the methods and bioreactors disclosed herein are not limited to using bacteria and Archaea to perform the biodegradation. For example, yeast, fungi and/or molds that biodegrades a carbonaceous material within bioreactor 20 may also be used.

As noted above, the stacked particle bioreactor 20 preferably starts as an aerobic bioreactor and is then converted to an anaerobic bioreactor. The anaerobic environment within bioreactor 20 may be formed, for example, by covering heap 30 with a gas impermeable barrier 36. Gas impermeable barrier 36 is preferably a clay barrier layer or a plastic liner.

Once the heap 30 is covered, unless additional air or oxygen is supplied to bioreactor 20, bioreactor 20 will naturally become anaerobic over time because all of the available oxygen will be consumed by the aerobic biodegradation of the carbonaceous material within bioreactor 20. As the available oxygen is consumed, the process within bioreactor 20 will convert from an aerobic biodegradation process to an anaerobic biodegradation process. To speed the conversion process up, oxygen can be purged from the bioreactor by sweeping or purging the bioreactor with a non-oxygenated gas such as argon, nitrogen, carbon dioxide, ammonia, hydrogen or combinations thereof, as well as any other anaerobic environment supporting gas. The biodegradation process will also benefit from the use of facultative anaerobic bacteria during conversion from an aerobic to an anaerobic environment within heap 30. This is because the facultative anaerobes can continue the degradation process while there is still too much oxygen in the environment to support the growth of obligate anaerobes, but insufficient oxygen for robust aerobic fermentation to continue.

Gas delivery system 60 may be used to deliver gas throughout the bioreactor. Gas delivery system 60 includes perforated pipes 31 that are buried within heap 30, preferably adjacent to the bottom portion of heap 30, at the time the heap is constructed. Gas delivery system 60 also includes pipe 62 which is in communication with perforated pipes 31 and selectively communicates, through valve 27, with air blower 28 or purging gas supply 64. Prior to converting the bioreactor 20 to an anaerobic system, valve 27 is preferably positioned to open communication between air blower 28 and pipe 62. As a result, air from air blower 27 can be delivered to the bioreactor 20 through perforated pipes 31 while aerobic biodegradation is being carried out within bioreactor 20. Thus, gas delivery system 60 may be used to adjust and control oxygen levels within the heap 30 as well as to control the temperature within the heap 30 during the aerobic phase.

Preferably, gas delivery system 60 is adapted so that it may also be used to deliver a purging gas to the bioreactor 20 in order to create an anaerobic environment within the bioreactor. In this regard, when bioreactor 20 is to be converted to an anaerobic reactor, valve 27 is preferably adjusted to close communication between pipe 62 and blower 28 (or atmosphere). In addition, however, preferably valve 27 may also be adjusted to open communication between pipe 62 and a source of purging gas 64. Once bioreactor 20 is sufficiently purged, valve 27 may be adjusted to a third position in which communication between pipe 62 and both blower 28 and purging gas supply 64 are shut off.

Gas collection system 33 may be used to collect and remove gaseous synfuel from the bioreactor 20. Gas collection system 33 includes a plurality of perforated pipes 68 positioned toward the upper portion of heap 30 during construction of heap 30. In addition, collection system 33 includes a means for communicating the collected gaseous fuel, such as pipe 70, to a holding tank 26. As the gaseous synfuel will typically contain a methane and carbon dioxide mixture resulting from methanogenic degradation, preferably the captured gaseous synfuel is processed through a separator 39 prior to storing the desired methane fuel values in holding tank 26. Separator 39 is designed to separate out carbon dioxide from the methane in the captured gaseous synfuel. Examples of suitable carbon dioxide/methane separation technologies are described in U.S. Pat. No. 4,518,399, which is hereby incorporated by reference. The separated carbon dioxide gas is preferably communicated via pipe 72 to conduit 62 of gas delivery system 60 and is thereby recycled to the bioreactor 20. Purified methane obtained from separator 39 may then be stored in holding tank 26 for subsequent sale or use.

Carbon dioxide from separator 39 is preferably recycled to the bioreactor 20 to maintain positive pressure within the bioreactor during the anaerobic phase, thereby helping to maintain anaerobic conditions by minimizing the chance for oxygen contamination. Furthermore, carbon dioxide is actually one of the substrates that methanogenic organisms use in the production of methane.

If the gaseous synfuel collected from bioreactor 20 has sufficient methane fuel values, it may alternatively be fed directly to gas-fired electric power generator 45. The gas-fired electric power generator may be driven by a gas turbine or internal combustion engine adapted to run off the collected gaseous synfuel. The power generated from the generator 45 may be used to provide electricity for other plant operations, sold to a local power company, or sold directly to consumers.

Due to the efficiency of engines and turbines, only a small percentage (24 to 38% for internal combustion engines and 16 to 18% for small turbines) of the methane fuel values burned will be transformed into electrical energy. The remainder of the fuel values in the burned methane gas will be converted to excess heat. However, if biodegradation power plant 10 is located near a coal, oil shale, or oil sand reserve, the excess heat produced by gas-fired electric power generator 45 may be used for a variety of purposes, including, for example, the production of steam and/or hot water for use in extracting petroleum-like products from oil sands, gasification of coal, and pyrolysis of oil shale; thus permitting the excess heat generated from power plant 10 to be used in conventional technologies for recovering oil from these fossil fuel resources.

While all portions of heap 30 are being aerobically biodegraded, only carbon dioxide gas will be produced. Accordingly, a valve 71, which may be provided in pipe 70, may be opened to vent the carbon dioxide produced within the bioreactor.

A variety of sensors 35 may be placed at one or more locations throughout heap 30 to measure oxygen levels within the bioreactor 20 during the biodegradation process. Sensors 35 may also monitor other process parameters, including temperature, ionic strength, sulfate concentration, toxic metal levels, pH, or Eh. Oxygen levels and other gases can also be measured by monitoring the gases traveling through gas collection system 33. Similarly, parameters such as temperature, ionic strength, sulfate concentration, toxic metal levels, dissolved oxygen, Eh or pH can be measured within the bioreactor by monitoring liquids removed from the bioreactor 20 via liquid collection system 32.

Liquid collection system 32 includes a drainage system 74 built into the lowest layer of heap 30. Drainage system 74 is adapted to remove liquids from the bioreactor 20 and includes a drain 80 from which fluids that drain from the heap 30 may be collected and recycled to the heap 30 or processed for their fuel values. In the present embodiment, drainage system 74 essentially comprises a series of French drains in that it comprises a series of generally parallel perforated pipes 76 oriented with their perforations toward the ground and buried in a layer of gravel 78. Liquids that drain through perforated pipes 76 collect in drain 80 where they are preferably communicated to an oil/water separator 37. Liquid synfuel produced in bioreactor 20 is removed from the top of separator 37 and water 66 from the bottom. The liquid synfuel is communicated to tank 25 for storage pending future use or sale. The recovered liquid synfuel may include a variety of hydrocarbons as well as alcohols, thus, it may be desirable to further refine the liquid synfuel prior to use or selling it on the market.

Water 66 recovered from separator 37 is preferably recycled to the bioreactor 20 through irrigation system 34, and to the extent necessary supplemented with additional inoculant and nutrients from supply 40. Inoculant within supply 40 may come from liquid taken from different operating heap as a means for introducing active and adapted microorganisms into heap 30. In addition to inoculant and nutrients, liquids introduced into the heap may have other agents added from supply 40 as the liquid is moved back into the heap. Additional additives may include, for example, water, buffering agents, sugars, waste oil, slurried cow manure. Preferably, contaminants and/or biotoxins are removed from water 66 recovered from separator 37 before the recovered water 66 is recycled to heap 30.

The stacked particle bioreactor 20 will continue to produce gaseous and/or liquid synfuel for a period of several months or years. The eventual yield of energy from the fossil fuels or other carbonaceous material included in the bioreactor, however, will be high because very little energy will be lost to the formation of carbon dioxide as an end product.

After bioreactor 20 is depleted of carbonaceous material, the bioreactor may be left intact. Alternatively, it may be desirable to aerate the bioreactor to completely remove all residual hydrocarbons or other carbonaceous material in the bioreactor. Finally, if the bioreactor is formed from coated substrates, which are discussed more fully below, the substrates may be recovered, recoated with more carbonaceous material, and stacked into a new heap.

Several preferred types of particles for forming heap 30 of bioreactor 20 are now described in connection with FIGS. 2-5.

In general terms, heap 30 is preferably made up of a plurality of coarse particles comprising a carbonaceous material. The particles preferably fall within a fairly narrow size range to ensure adequate fluid flow, particularly liquid flow throughout the heap. The use of substantially uniform size particles to form a particular heap 30 will allow the uniform flow of liquid or gas through the bioreactor. Wider size distributions, on the other hand, will cause packing and reduction of void volume. The void volume in the heap should generally be greater than or equal to about 15%, and more preferably greater than or equal to about 20%. Typically, the void volume will be in the range of 15 to 35%. More preferably, the void volume will be in the range of 20 to 30%. Uneven packing or size segregation may cause uneven flow of gas and liquid within heap 30 and reduce the ability to control the uniform flow of liquid or gas within the stacked particle bioreactor 20.

The particles used to form heap 30 should also have sufficient integrity to be able to withstand the anticipated compression forces that will be encountered within heap 30. Typically, this will mean that the particles should have the ability to withstand the force of many tonnes of material stacked on top of them. And, while the particles are preferably of a generally uniform size to promote fluid flow within bioreactor 20, they also preferably have a rough, nonuniform surface morphology to help increase the total surface area of the bioreactor 20.

Three methods of achieving particles with suitable characteristics for practicing the methods disclosed herein are described in U.S. Pat. Nos. 5,766,930, 5,431,717, and 5,332,559, which are incorporated herein by reference.

Figure 2:
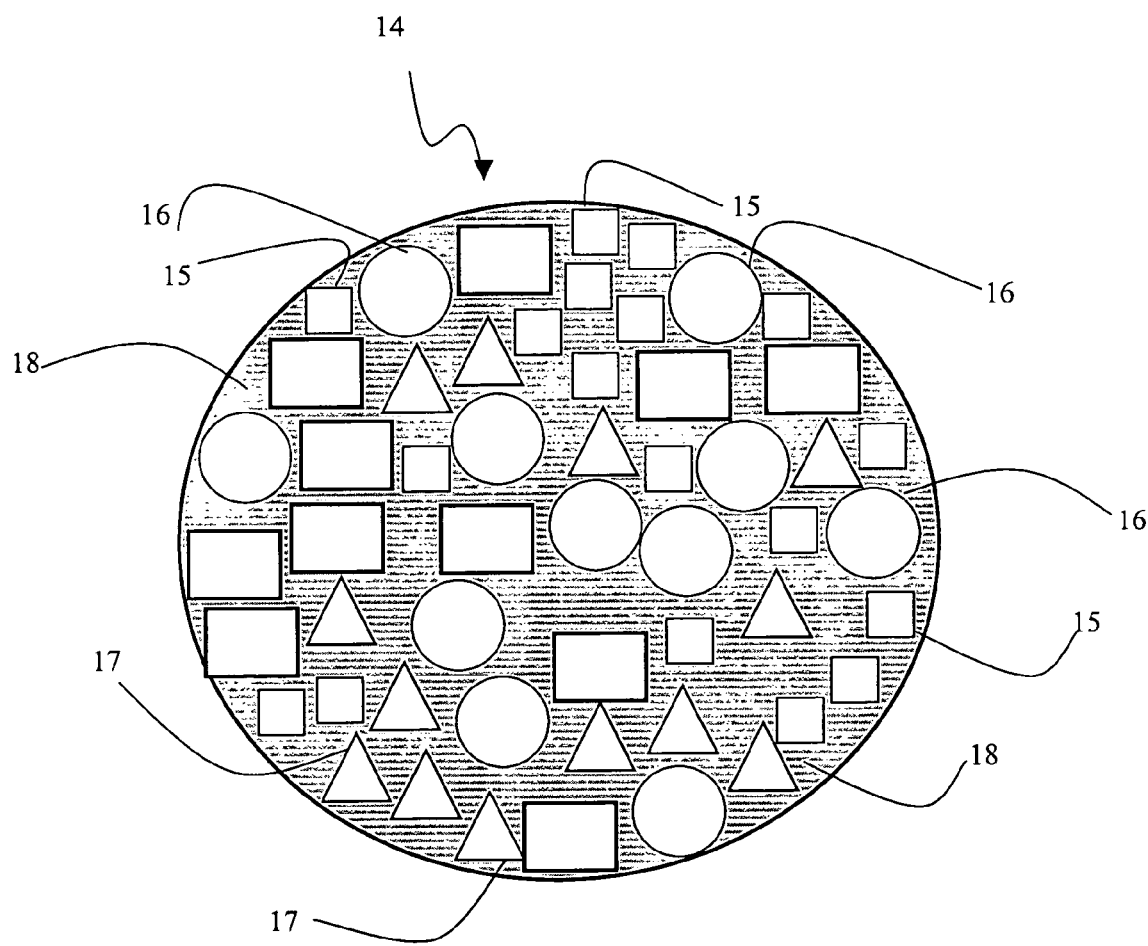
FIG. 2 is a cross sectional view of an agglomerated particle of one or more types of organic carbonaceous materials held together with a binding agent.

Agglomeration of crushed particles is one approach to increasing particle size and thereby improve percolation of liquid through the heap. FIG. 2 shows a cross sectional view of an agglomerated particle 14, a plurality of which may be used to form heap 30. The agglomerated particle 14 is comprised of a plurality of smaller particles 15, 16 and 17 held together by a binder 18. The smaller particle 15, 16 and 17 may comprise fines generated from crushing a biodegradable carbonaceous material. Alternatively, smaller particles 15, 16, and 17 may comprise particles from two or more different sources of carbonaceous material that have been combined together to make the agglomerated particle 14. Thus, it may be desirable to combine particles from two or more carbonaceous materials having different biodegradation characteristics to improve the overall biodegradation process within bioreactor 20. It may also be desirable to coat the plurality of agglomerated particles 14 with additional carbonaceous material. For example, the agglomerated particles 14 used to form heap 30 may be coated with a slurry created from biomass from ethanol fermentations, municipal waste sludge, or agricultural waste to provide nutrients to the biodegrading microorganisms present in the heap.

Agglomeration should be considered when the biodegradable carbonaceous material to be biodegraded includes a significant fraction of particles less than about 0.3 cm in diameter. Following agglomeration, preferably the agglomerated particles 14 have a particle size in the range of about 0.3 cm to about 2.54 cm. In this regard, if the carbonaceous material is particularly fine grained such that it is less than about 250 µm in size, then the coating process discussed below may be a more appropriate particle fabrication option.

Figure 4:
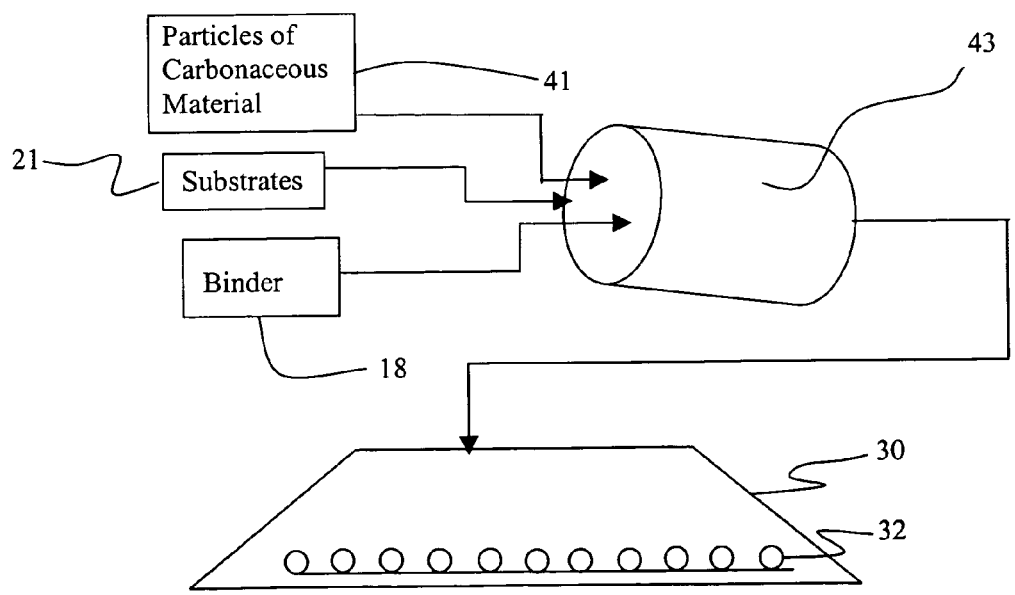
FIG. 4 is a schematic illustration of a process for producing agglomerated and/or coated particles.

A means for producing the above mentioned agglomerated particles 14 is illustrated in FIG. 4. Particles of carbonaceous material 41 that are to be agglomerated are fed into a rotating drum 43 along with an appropriate amount of binder 18. The binder 18, for example, may be lime, Portland cement or any suitable polymeric binding agent used in the mining industry. Alternatively, it may be possible to use another hydrocarbon source such as asphaltic oil, waste oil, bitumen, tar, pitch, or kerogen as binder 18, but at a minimum such materials may be added as a coating on the agglomerated particles 14.

Suitable binding agents will be those materials that bind the particles of carbonaceous material 41 together into a plurality of relatively uniform sized particles 14 and that produce particles that are strong enough to withstand the weight of the heap. Further, the resulting agglomerated particles 14 must be compatible with the pH of the biological process and not prevent the access of the microbes to the carbonaceous material to be degraded and converted to liquid and gaseous synfuel. The methanogenic and fermentative microorganisms used in the preferred embodiments of the present invention can grow in the pH range of 6 to 8 and are thus compatible with Portland cement and other neutral to alkaline pH agglomeration aids. Because microbial degradation of carbonaceous materials produces organic acids that can lower the pH out of the optimal range of 6 to 8, however, the use of cement as a binder may help maintain the optimal pH range for the methanogenic anaerobes. The primary advantage of Portland cement type agglomeration aids though is their strength and thus non-compressibility of the particles 14 when cement is used as the binder 18.

Once the agglomerated particles 14 are formed, they can be stacked into a heap 30 and used in the bioreactor 20 disclosed herein.

Figure 3:
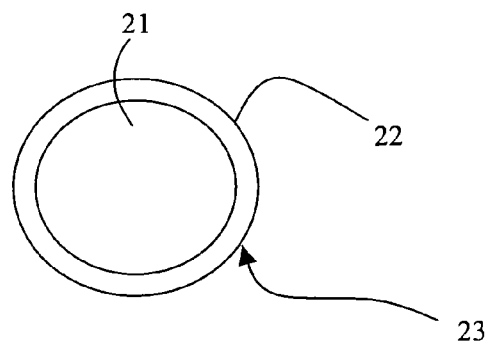
FIG. 3 is a cross sectional view of a coated particle that may be used to form a support and a coating of a carbonaceous material.

FIG. 3 illustrates a cross sectional view of a coated particle 23, a second type of particle that may be used in the present invention. In this embodiment, particles of carbonaceous material 41 are coated onto a plurality of substrates 21 to form a plurality of coated particles 23 having a coating 22 of carbonaceous material. Alternatively, the coating 22 may include or be formed from a liquid carbonaceous material. The particles of carbonaceous material 41 and/or liquid carbonaceous material may be coated onto the substrates 21 using a variety of techniques, including the use of rotating drum 43 as shown in FIG. 4 or a high pulp density slurry sprayer.

The substrates 21 are preferably solid and preferably have particle size greater than or equal to about 0.3 cm and less than or equal to about 5 cm. More preferably substrates 21 have a particle size greater than or equal to about 0.3 cm and less than or equal to about 3 cm. While the coarse substrates 21 preferably have a particle size greater than about 0.3 cm, it is recognized and contemplated that some of the substrates may actually be smaller than this particle size. As those skilled in the art will recognize, if the coarse substrates 21 are produced by crushing larger material to the desired size range, the crushed material will have a certain size distribution. And even if the material is screened to exclude material less than about 0.3 cm, some material having a particle size less than the 0.3 cm target minimum will still be present in the coarse substrates due to inherent inefficiencies in the screening process and due to particle attrition during handling. Thus by greater than or equal to about 0.3 cm it is intended that substantially all of the coarse substrates are above this size so that the void volume of the reactor remains above at least about 20% during formation of heap 30 and, preferably throughout its operation. Preferably the amount of coarse substrates below the 0.3 cm cutoff is less than 5% by weight.

It is desirable to form a relatively uniform coating 22 of the particles of carbonaceous material 41 on the substrates 21 to maximize the integrity of the coating and the surface area of the particles 41 exposed to the microorganisms in the bioreactor 20. Further, as the particle size of particles 41 decreases, the biodegradation process will proceed more quickly. Smaller particles will also tend to stick better to substrates 21. In view of this, the particle size of the particles of carbonaceous material 41 is preferably less than about 250 µm, and more preferably the nominal particle size of the particles of carbonaceous material 41 to be coated on substrates 21 is greater than about 75 µm and less than about 106 µm. The thickness of the coating material is preferably less than 1 mm to ensure that the microorganism(s) being used to perform the biodegradation have adequate access to all of the carbonaceous material being treated.

The total surface area of the bioreactor 20 can also be increased by decreasing the particle size of substrates 21, using substrates 21 that have a rough, nonuniform surface morphology and/or increasing the number of coated substrates 23 stacked on the heap 30. The advantage of increasing the total surface area of the substrates within the heap is that the amount of carbonaceous material that can be loaded on substrates 21 in coating 22 increases proportionately, which in turn increases the amount of carbonaceous material that can be degraded into liquid and gaseous fuel.

The coated particles 23 may be produced using a variety of techniques. One possibility is to add substrates 21 and particles 41 to a rotating drum 43 in appropriate quantities. Preferably the substrates 21 are dry and particles 41 are in a high pulp density slurry so that it will stick to substrates 21 to form coating 22. Alternatively, both substrates 21 and particles 41 may be added to rotating drum 43 dry and then water and/or other binding agent may be sprayed into the rotating drum 43 to promote adhesion of the particles 41 to the substrates 21.

An alternative method of forming coated particles 23 comprises spraying particles of carbonaceous material 41 in a high density slurry onto substrates 21 before, or as, the substrates are being stacked to form heap 30 of bioreactor 20.

A neutral to alkaline pH resistant binder 18, such as Portland cement may be used to help hold the coated particles of carbonaceous material 41 onto the solid substrate 21. However, the particles of carbonaceous material 41 coated on substrates 21 may also be applied to the substrate without a binder as well, if substrates 21 and particles 41 are sufficiently hydrophobic. An advantage of this latter approach is that the cost of a binding material may be avoided. A liquid or semi-liquid hydrocarbon may also be used to hold particles 41 to substrate 21 to form a coating 22 with sufficient structural integrity. Thus, for example, asphaltic oil, waste oil, bitumen, tar, pitch, and/or kerogen may be used to bind particles 41 to substrates 21. Or the coated particles 23 may be further coated with such substances to further increase the content of carbonaceous matter within bioreactor 20.

The advantage of using a plurality of coated particles 23 to form heap 30 over using agglomerates 14 is that the solid substrate 21 of the coated particles 23 provides high strength to maintain the shape of the particle. Another advantage of this embodiment is that the coating 22 may be a softer hydrocarbon or biomass that could not be agglomerated into a particle with sufficient strength to withstand compression, but can withstand compression when coated onto a substrate. Thus, by coating the softer material onto a solid support the permeability in very large heaps can be maintained. Another advantage is that the outer coating of hydrocarbons will be fully accessible to microbes for conversion to liquid fuel, oil and/or methane.

The substrates 21 may be created from any number of materials that are capable of withstanding the weight of the stacked particles. Examples of suitable substrates 21 that do not contain any practical concentration of carbonaceous material include barren rock, gravel, lava rock, barren rock containing carbonate minerals, brick, cinder block, and slag. Preferably, however, substrates 21 also comprise a biodegradable carbonaceous material that will also eventually be converted to either oil or methane. In this regard, the plurality of substrates may comprise, for example, one or more materials selected from the group consisting of oil shale, coal, rock, asphalt, rubber, and plant waste. Examples of suitable plant waste that may be used as substrates 21 include, for example, plant waste selected from the group consisting of bark, corn cobs, nut shells, wood by-products, and crop by-products. Coal substrates may comprise any of the true coals, including semianthracite coal, semibituminous coal, bituminous coal, subbituminous coal, and lignite coal.

The particles of carbonaceous material 41 coated on the substrates 21 may comprise, for example, an organic carbonaceous material selected from the group consisting of oil sands, oil shale, asphaltic oil, waste oil, bitumen, tar, pitch, kerogen, coal and agricultural waste. Further, the types of agricultural waste that may be coated on the substrates include, for example, manure, fruit waste, straw, fermentation waste, and pulverized plant waste. Grape skins are a particularly preferred form of fruit waste that may be coated on coarse substrates for biotreatment. In addition, rice straw is a particularly preferred form of straw that may be coated on the substrates for biotreatment. If coal is used as the organic carbonaceous material coated on the substrate, preferably the coal has a metamorphic rank of bituminous coal or less, and more preferably a metamorphic rank of peat or less. Moreover, if the organic carbonaceous material coated on the substrate comprises coal or oil shale, preferably the coating is a concentrate of those materials.

In a particularly preferred embodiment, the particles of carbonaceous material 41 forming coating 22 comprise a carbonaceous material that is readily biodegraded, such as biomass or agricultural waste, and thereby accelerates the overall process by providing large amounts of fatty acids to be converted into methane by the methanogenic microorganisms within bioreactor 20.

Figure 5:
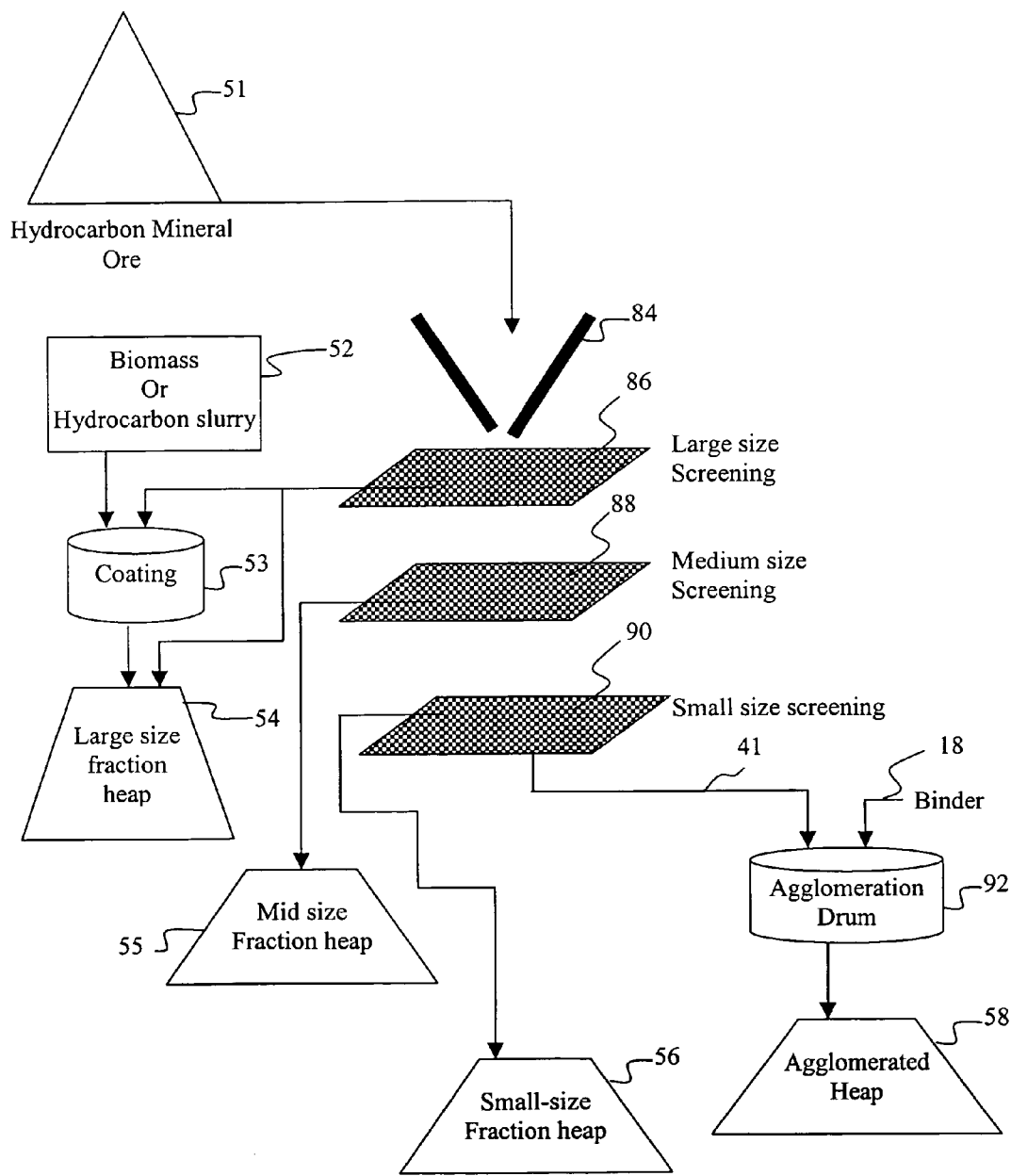
FIG. 5 is a schematic illustration of a process for forming a plurality of bioreactors according to the present invention.

A third method of producing particles of uniform size is illustrated in FIG. 5. In this embodiment, finer particles are removed to enhance air and liquid flow within the heap 30. Crushing and screening can remove the fine material from the crushed carbonaceous material. By removing fines before stacking, the size distribution is narrowed and thus air and liquid flow through the heap improved over the flow characteristics of the entire crushed material. In addition to removing the fines, the crushed rock can be further separated by size fractions. The various size fractions can then be stacked into separate heaps 30 or layers within a heap as discussed more fully below in connection with FIG. 5.

In a preferred embodiment, a carbonaceous material, such as a hydrocarbon mineral ore 51, is crushed in an ore crusher 84 to a size of about 5 cm or less. The crushed ore is passed through a set of screens 86, 88 and 90 which separates the crushed material into two or more size ranges. The size fractions might, for example, be separated as follows: a largest size fraction being 3 to 5 cm, a mid size fraction being 1 to 3 cm, a small size fraction being of 0.5 to 1 cm, and a fines fraction being 0.5 cm and less. The first three separated fractions of crushed material may be stacked into separate heaps according to fraction size. Thus, in the present embodiment, three heaps are formed: heap 54 for the large size fraction, heap 55 for the mid size fraction, and heap 56 for the small size fraction. The carbonaceous material in the fines fraction (e.g., the carbonaceous material less than 0.5 cm in size) might be too small to stack into a heap without first agglomerating the fines. Accordingly, as shown in FIG. 5, the particles of carbonaceous material 41 in the fines fraction may be agglomerated in an agglomeration drum 92. The agglomerated particles 14 from agglomeration drum 92 may then be stacked to form heap 58 of agglomerated particles.

The formation of agglomerated particles 14 in agglomeration drum 92 may be accomplished in the manner described above in connection with FIGS. 2 and 4. The fines fraction may also be further ground and then floated to form a higher-grade carbonaceous material. The resulting flotation concentrate may then be agglomerated in agglomeration drum 92 to form agglomerated particles 14 or coated back on the surface of the solid crushed and sized material to form coated particles 23.

Another way of treating the fines fraction is to treat that fraction separately from the heap bioreactor processes altogether. For example, the fines fraction may be treated in a conventional high temperature process, such as in a retort.

Although the fines fraction of the present embodiment is set at 0.5 cm and below, in other embodiments it may be set differently. For example, in some implementations, it may be desirable or sufficient to set the fines fraction at particles having a particle of about 0.3 cm or less.

The size fractions of carbonaceous material collected from various screens, such as the large size screen 86, may be able to hold a coating 22 as shown in FIG. 3. The carbonaceous material coated on the size fraction may be coated on the plurality of substrates 21 making up the size fraction in coating drum 53. The resulting coated particles 23 may then be stacked, for example, in heap 54. The various types of carbonaceous materials that may be coated on the particles in the various size fractions are fully described above in connection with FIG. 3. However, it is worth noting that the coating material may be a softer carbonaceous material than the hydrocarbon mineral ore being used as the substrate. For example, the carbonaceous material used as the coating material may be, for example, biomass, a hydrocarbon slurry, biomass from ethanol fermentations, municipal waste sludge, or agricultural waste.

Each heap 54, 55, 56, and 58 (or each layer if a stratified layer approach is taken) will have better flow characteristics separately than it would have if mixed together. If mixed together the smaller size material will fill in the void spaces, thereby reducing void space and restricting flow. In addition to reducing the void space some areas will inevitably have less fines and thus more void space and better flow than others. This disparity in flow rates will lead to channeling and non-uniform flow around the area with excessive fines and restricted flow. This is problematic when trying to purge oxygen out of the system or introduce a new culture of anaerobic microorganisms.

The smallest size fraction material will have the fastest rate of degradation. Yet, if this fraction is stacked separately in heap 56, it will still have uniform gas and liquid flow characteristics. The larger sized material will have better flow characteristics but slower rates of conversion to methane. The larger size fraction heap could also be used as a support rock for a coating of softer and more readily biodegraded material as described above. Also, large size fractions would have larger void spaces and could withstand more compression and, therefore, be capable of being stacked higher than the smaller sized material. The ability to withstand more compression would make it possible to stack the finer material as a layer on top of the larger size material. If stacked separately, each heap will generate oil or methane at different rates. Once a heap is no longer producing methane at an economical rate, a new heap may be formed on top of it. At that point, it would not matter if the remaining material in the original heap is compressed to the point that permeability is lost. As a result, this may be the least expensive way to produce high strength particles for large heaps. Further, the larger size particles would not need to be re-crushed to the smaller size ranges, which would also generate more fines and increase cost. And, although the larger size range material will biodegrade more slowly, because it will be able to be stacked in higher and larger heaps, heaps formed from larger size fractions of material may actually be able to produce the same amount of methane per square foot of land occupied as heaps formed from smaller size fractions.

Crushing hydrocarbon mineral ore 51, such as coal or oil shale, to a target maximum size in the range of approximately 0.5 to 3 cm may be readily accomplished using techniques widely known in the art. The ultimate maximum target size of the crushing operation, however, will depend on the rate of biodegradation and the time that the heap is expected to produce a liquid or gaseous fuel. As the size of the particles are made smaller the surface area available to the microbial degradation becomes larger. However, smaller crushing size targets increase crushing cost and the amount of fines that are too small to be included into the heap without agglomeration or coating as described above.

As will now be appreciated, the biodegradation process according to the present invention, and illustrated in FIG. 1, is useful for forming a large ex situ bioreactor while insuring adequate microorganism access to the carbonaceous material to be bio-converted into useful liquid and gaseous fuel or synfuel. Further, the enhanced liquid and gas flow provided by the preferred embodiments allows for the easy removal of liquid hydrocarbon fuels, such as synthetic petroleum, or gaseous hydrocarbon fuels, such as methane. The enhanced flow also allows for microorganisms and nutrients to be introduced into the bioreactor at any time after the formation of the heap. As illustrated in FIG. 1 and described above, means may be provided at the bottom, top, and throughout the heap 30 to facilitate the introduction and removal of liquids and gases.

The present invention also provides a cost effective way to achieve a very large, high surface area reactor for aerobic and/or anaerobic degradation of carbonaceous materials to synfuel. Indeed, it is possible to cost effectively scale the methods and bioreactors of the present invention to process thousands of tonnes of oil shale or oil sand per day. A typical commercial development of this invention may involve, for example, stacking 10,000 tonnes or more per day of carbonaceous material into heaps of up to a million or more tonnes of carbonaceous material total. The ability to cost effectively scale the methods and reactors of the present invention to a very large scale is important, not only because the conversion process will be slow, but also because it will be necessary to extract the fuel values from significant quantities of carbonaceous material to make a material impact on the world's petroleum supply. To put this in perspective, it would, for example, be necessary to extract the fuel value from approximately 100,000 to 400,000 tonnes of oil shale per day to replace about 1% of the US's current 10 million barrels of oil imported each day.

In light of the foregoing advantages, the methods and bioreactor designs described in the instant patent document are particularly well suited for deriving synfuel from low-grade fossil fuels. This is because it is possible with the methods and reactors of the present invention to process large quantities of such fossil fuels in a very large, low-cost process, which is crucial considering the long residence times that will be necessary to biodegrade those fossil fuels into synfuel and the concentration of energy values in those fossil fuels per tonne of material. Because oil shale, oil sands, peat and low-grade coal tend to be closer to the surface, however, they will tend to be relatively inexpensive to mine, thus keeping the costs of building the bioreactor relatively low in comparison to the recoverable fuel values added to the bioreactor. On the other hand, deeper deposits of carbonaceous rock will cost more to mine, thus potentially impacting the economics of the process negatively even though the mined carbonaceous rock may be of higher grade.

In considering the potential value of the present invention, and its economics, it is worth reviewing some noteworthy facts regarding some of the low-grade fossil fuels that may be processed in the present invention.

Oil shale—The total world resources of oil shale are estimated at over 2.6 trillion barrels of oil, with one of the largest deposits being located in the U.S. Thus, reserves of oil locked in oil shale dwarf known petroleum reserves by several time over. Oil shale typically contains 10 gal or more of oil per tonne of shale, with large quantities of shale in the U.S. containing over 20 gal/tonne or even 30 gal/tonne. Indeed, it is estimated that in the Green River formation in the U.S. there are 731 billion barrels of oil in shale reserves that contain at least 25 gal of oil per tonne of shale. If such shale can be processed for a price of $5 per tonne or less, the process will clearly be economical. Considering, however, that the cost of processing a tonne of ore in heap bioleaching techniques in the mining industry is in the range of $2 to $5 per tonne, processing shale at a cost of $5 or less per tonne is very feasible.

Oil sands—Oil sands of the world contain the largest accumulations of liquid hydrocarbons in the earth's crust. Sometimes called tar sands and bituminous sands, oil sands contain a heavy viscous petroleum substance called asphaltic oil. The largest reserves of oil sands in the world are located in Alberta, Canada, which have been estimated to contain over one trillion barrels of oil. Another deposit of oil sands in South America is said to contain 692 billion barrels of oil. Oil sands typically contain from 0.5 to 1 barrel of oil per tonne.

Low rank coal—The U.S. has significant reserves of low rank coal, such as brown coal and peat, as well as other humic substances. Moreover, the U.S. has the world's largest peat reserves. Peat has a persistently high moisture (minimum 75%), which typically requires it to be dried before it is burned in other processes. Peat may be used in the present process, however, without drying it first, thus saving a substantial amount of money in processing this resource.

High sulfur petroleum and coals—Due to environmental restrictions on sulfur dioxide emissions these fossil fuels can only be burned in plants having adequate pollution control systems or the sulfur must be removed prior to burning the fuels. In the present invention, however, high sulfur fossil fuels may be readily processed.

A preferred embodiment for producing and recovering a liquid hydrocarbon fuel from tar sands or oil sands and oil shale is provided. Tar or oil sands and oil shale contain a large amount of hydrocarbons. Some portions of the hydrocarbons can be washed off or removed with water and elevated temperatures. In addition, products of aerobic microbial fermentation of these hydrocarbons will aid in the removal of the hydrocarbon. For example, microbes of the genus *Arthrobacter, Bacillus Corynebacterium, Pseudominass* and others listed in Table 1 above produce surfactants and solvents that will aid in dislodging oil held on the surface of the sand and shale of these hydrocarbon sources.

In addition to these microbially produced extraction agents, microbes are capable of reducing the molecular weight of paraffinic hydrocarbons and thereby lowering their viscosity. The resulting lower viscosity oil may then be removed more readily from the sand and shale by water flow.

Thus, the biological process of mobilizing oil is a way of enhancing the extraction of oil contained within the oil sand or oil shale. In addition to producing extraction agents useful in the separation of hydrocarbon values from minerals, the microorganisms convert the hydrocarbons to lower molecular weight petroleum oil. Further, the aerobic microorganisms used to produce extraction agents and reduce the viscosity of the oil will produce, through further biodegradation, small organic molecules which may be subsequently consumed by methanogenic microorganisms and converted to methane and carbon dioxide. While microorganisms available from culture collections may be used, wild type microorganisms isolated from the hydrocarbon site itself are likely to be the most useful to include in the heap culture.

The released oil may subsequently be extracted from the minerals in the heap using the broth from the aerobic fermentation. As described above, the oil mobilization bacteria can be added to the heap of agglomerated oil sand or oil shale as the heap is being formed or shortly thereafter. This aerobic part of the process starts the mobilization and viscosity reduction of the heavy hydrocarbons and tars into removable oil that is eluded out of the heap by the flow of liquid through the heap particles and into the liquid collection system 32 where it is then provided to oil/water separator 37, and the separated oil collected in tank 25.

After the heap is covered or sealed the process can be converted to an anaerobic environment by sweeping bioreactor 20 with carbon dioxide or by letting the aerobic microbes consume the entrapped oxygen. The process of oil removal may still continue because anaerobic microbes can still mobilize oil by producing surfactants and solvents.

As the heap becomes anaerobic, methanogenic microorganisms are introduced into the heap 30 through irrigation system 34 to start generating methane. These strictly anaerobic microorganisms can be obtained through culture collections, some of which are listed in Table 2. In addition to obtaining methanogens from culture collections, mixed culture can be isolated under anaerobic conditions from peat bogs, sewage treatment plants, rice paddies, and the intestinal tracks of ruminants. In this part of the process the residual hydrocarbons and organic compounds produced by the aerobic part of the process are converted to methane. In addition, during this part of the process the oxygen level and other parameters such as temperature, pH, solution chemistry, sulfate levels, and toxic metals should be monitored using sensors 35 or other means discussed above. Adjustments can be made to the heap environmental conditions by controlling the gas and liquid flow to the heap via gas delivery system 60 and irrigation system 34.

The anaerobic phase of this process will take longer than the aerobic phase of the process. Further, the surface hydrocarbons on the particles that make up the bioreactor will be converted to oil and methane fastest. Later in the process, the microbes will consume the more embedded hydrocarbons within the particles. The total time and rate of methane generation will be a function of the size, distribution of the particles and the biodegradability of the carbonaceous material. Most coal, for example, will biodegrade anaerobically to methane, but at a very slow rate. A solid support made of low-grade coal may take several years to be converted to methane. A layer of tar sand coated onto the solid coal support may be converted to liquid oil and methane within the first year of the process. A layer of biomass or agriculture waste coated onto coal support may be converted to methane in a few months. The rapid growth of microbes on the outer layer of more susceptible organic material will facilitate the biodegradation of the more resistant solid support by accelerating the rapid development of a thick coating of actively growing microbes over all the solid support particles.

After the outer layers are degraded and most of the easily accessible hydrocarbons are converted to oil or methane the need for void space and good flow characteristics within the heap are diminished. Therefore, new heap bioreactors may be constructed on top of the older heap bioreactors that have consumed most of the outer softer material. At that point, the older heap in the slower part of the methane generation cycle may be better able to accommodate the extra weight of another heap or lift built on top of it.

The following prophetic examples further define the invention and should not be construed as limiting the invention to the examples set forth. For example, the specific examples described below are directed at biodegrading oil shale, oil sand, coal, and peat. However, as described above, the device and method according to the present invention may be used to biodegrade all types of biodegradable carbonaceous materials.

EXAMPLE 1

In this example, a solid hydrocarbon containing material such as oil shale is used in a heap bioreactor 20 to produce both oil and methane. The oil shale is mined and crushed to a size of less than 5 cm with an average size fraction of about 3 cm. As illustrated in FIG. 5, the smaller size fraction of less than about 1 cm is agglomerated into larger particles of about 3 cm. A polymeric or Portland cement binder 18 may be used to help form stable agglomerates. It is recognized that another hydrocarbon source such as tar or high viscosity oil may act as a suitable agglomeration aid or may be coated on the surface of the agglomerate. Another way of treating the fines is to remove them from the heap process altogether. Further grinding and flotation may be used to form a higher-grade hydrocarbon that can then be agglomerated or coated back on to the solid crushed and sized material. Alternatively, the fines fraction may be processed in a conventional high temperature process, such as in a retort.

The size of the particles is chosen by a compromise between cost and the rate of oil and gas production. The smaller size range of 1 to 3 cm will give faster oil and methane production. The large size range 3 to 5 cm will cost less to crush and produce less of the fines that will need to be removed or agglomerated. A mixture or larger size range of 1 cm to 5 cm will pack more tightly and restrict gas and liquid flow. It would be better to stack two separate heaps or lifts of two size ranges (1-3 cm and 3-5 cm) than to combine them. Therefore, it is beneficial to test each of the sizes or size ranges to determine the relative rates of organic carbon and hydrocarbon degradation and extraction and methane generation. This may be done in a small-scale laboratory test for each type of hydrocarbon mineral to be processed at commercial scale. This type of test will determine the rate of oil and methane production with time. Microbes used in the test and the environmental conditions such as temperature, pH and nutrients will also affect the rate.

As the agglomerates are being made, or as the heap is being stacked, a consortium of hydrocarbon degrading microbes is added to the heap. The consortium should be a mixed culture of microbes of aerobic and facultative anaerobic microorganisms that are known to degrade hydrocarbons of the type being treated in the heap process. More specifically, the mixed culture should be adapted to feed on the hydrocarbon source being treated in the heap. Methods of isolating and adapting microorganisms for hydrocarbon degradation of petroleum oil are generally known by those skilled in microbiology. One method of microbe adaptation is taught by Ikeda et al. in U.S. Pat. No. 5,919,696, which is hereby incorporated by reference.

The heap will be aerobic during the time that it is being stacked. Perforated pipes 31 and 76 in gas delivery system 60 and liquid collection system 32, respectively, are laid down first and covered with rock or the heap particles directly. As the heap is stacked higher, irrigation system 34 and gas collection system 33 are placed in the heap. These may be at the top and midsection of the heap. Sensors 35 may be added to the heap 30 to monitor various process parameters, including temperature, oxygen concentration, pressure and pH, and transmit the detected information to controller, not illustrated herein.

In the aerobic phase of the process microbes feed on the hydrocarbons to produce bio-surfactants, solvents, and heat that help dislodge and mobilize the petroleum contained in the oil shale. In addition, the microbes bring about chemical changes to the viscous hydrocarbons that reduce the viscosity of the oil contained in the shale. This oil migrates to the lower part of the heap to be removed by the liquid collection system 32. Water may also be used as a carrier to help sweep the oil off of the stacked particles. The aqueous solution and oil are then collected in an oil/water separator 37 where the oil can be separated from the aqueous solution and then provided to tank 25 for storage. The separated water may then be circulated back into the heap through irrigation system 34. Alternatively, the water can be removed as waste.

The aerobic process may continue after the heap is stacked and covered with an impermeable liner 36, for example a clay cap or plastic liner. The length of time will depend on the material being processed and the economic value of liquid oil vs. methane. The process is changed from an aerobic process to an anaerobic process by stopping the flow of air through the gas delivery system 60 built into the heap or by sweeping the heap with a low oxygen (less than 1.0%) gas mixture. A possible gas mixture could be nitrogen and carbon dioxide. The aerobic microbes will break the higher molecular weight hydrocarbons to smaller molecules. This will help the start of methane generation during the anaerobic process. However, the aerobic process will waste more of the energy potential of the hydrocarbon fuel by degrading the hydrocarbon all the way to carbon dioxide, water and heat. Economics will determine the best time to convert the heap from the faster aerobic process to the slower anaerobic methane generation process.

Careful control of oxygen levels may be needed to optimize methane generation without hydrogen sulfide generation. Sulfate reducing bacteria will compete with methanogenic microbes for the acetate, fatty acids and hydrogen produced by fermenting anaerobic microbes. The sulfate reducing bacteria will produce hydrogen sulfide and not methane, thereby decreasing the efficiency of the process.

Strictly anaerobic methanogenic microorganisms may need to be supplied to the heap after it has become anaerobic because they may not have been able to survive the aerobic part of the process. These methanogenic microorganisms may be obtained from an existing heap operating in the anaerobic mode, as such a heap is a source of adapted and actively growing microorganisms. During the anaerobic phase liquid oil may still be produced and collected. The methane gas is produced until most of the available hydrocarbon has been converted to liquid petroleum/oil or methane. The time will depend on the size of the particles or the crush size of the shale being processed. A smaller crush size than 5 cm will cost more to produce but will produce oil and methane faster. Experimentation and economic analysis can determine the best crush size for a particular shale.

EXAMPLE 2

In this example the hydrocarbon source is oil sand. This material is also called tar sands and contains bitumen similar to oil shale. Alberta Canada has three of the world's largest oil sand deposits, which are conservatively estimated at over one trillion barrels. Bitumen makes up about 10-12% of the oil sands. The remainder is 80-85% sand and clay minerals and 4-6% water. Only about 10% of these deposits are considered recoverable with conventional hot water extraction or flotation enrichment technology. These non-biological extraction processes leave about 25% of the bitumen in an alkaline tail.

In this example, the oil sands material is agglomerated into small pellets or particles of about 1 to 3 cm in size. The size of the particles biotreated should be selected based on the rate at which microbes will reduce the viscosity of the heavy oil and extract it from the particles. This can be determined in laboratory experimentation as was done in Example 1. In general, smaller particles will yield more oil at a faster rate than the larger particles. However, the smaller particles may be more expensive and difficult to produce.

In addition to determining the appropriate particle size, the appropriate amount and type of binder may be experimentally determined using techniques known in the mining art. The selected binder should be strong enough to hold an agglomerated particle 14 together and resist the weight of the heap. The amount of the binder used, however, should not be so much that the penetration of microbes or extraction of oil is prevented. Also the use of excess binder will increase the cost of the process. Suitable binders include, for example, Portland cement and polymers. Flotation concentrate of bitumen may also be agglomerated into the particle or coated onto the outer surface of the particle. The amount of cement used will typically be in the range of about 1 to 3%.

The agglomerated particles 14 are inoculated with an adapted consortium of microbes that are capable of reducing the viscosity of bitumen and converting it to lighter molecular weight oil. This consortium should be a mixed culture of aerobic and facultative anaerobic microorganisms that are known to produce surfactant solvents and heat that help dislodge the oil. The mixed culture should also contain thermophiles that can survive the higher temperature that results from the heat released by the aerobic hydrocarbon degradation. The heap should be designed and operated to conserve the heat generated because it will aid in the oil extraction.

The heap will start as an aerobic process as in Example 1. Gas delivery system 60, irrigation system 34, and liquid collection system 32 may be built into the heap to inject process gas and water and collect drainage water that contains extracted oil and process water. As the heap is stacked higher, irrigation system 34 and gas collection system 33 are placed in the heap. The process water collected in liquid collection system 32 is separated from the oil in oil/water separator 37 and then reconditioned for re-injecting and reuse through irrigation system 34. The reconditioning step may include pH adjustment and removal of toxic materials that may retard bacterial growth. Also new microbes could be added to this process water. Those might be strictly anaerobic fermenting and methanogenic microbes for the production of methane.

In addition to the irrigation system and liquid collection pipes, the heap is constructed with gas supply and removal pipes 31, 68. The supply pipes 31 are necessary to inject gas mixture that can control oxygen levels within the heap. During the aerobic part of the process the oxygen level can be from 1-10% or more to stimulate bitumen degradation and conversion to liquid oil. After most of the recoverable oil is removed, the oxygen level is reduced to facilitate methane generation. The remaining oil and low molecular weight organic compounds and the aerobic microbes themselves are quickly converted to acetate and other one or two carbon compounds by anaerobic fermenting microbes. Anaerobic methanogenic bacteria then convert these compounds into methane, which is collected through the gas collection system 33.

The process then proceeds more slowly as the anaerobic consortium of fermenting and methanogenic microbes continue to degrade the higher molecular weight bitumen or other organic hydrocarbon sources. This slower process may go on for several years. The gas generated will contain a mixture of methane and carbon dioxide. A more highly concentrated methane gas can be produced by removing the carbon dioxide from the gas mixture means of separator 39. The purified methane gas can be sold as natural gas. Alternatively, if not already of sufficient concentration in pipe 70, the gas can be cleaned up enough to be burned in electric power generator 45 to provide heat and/or electricity.

EXAMPLE 3

The U.S. and other countries throughout the world have vast amounts of mineable coal. Unfortunately, many of these sources of coal are of low grade or are high in sulfur or ash and are not useful for power generation for environmental reasons. Stricter air quality requirements have reduced the usefulness of many of these coal sources. Most new power generating plants are designed to use cleaner burning natural gas.

In this example, low-grade coal is converted to cleaner burning methane gas by anaerobic bioconversion of coal to methane in a large ex situ heap 30 of crushed and sized coal. The solid nature of coal and its complex chemical structure make it slow to be microbially converted into methane. Thus, in addition to inoculating with fermenting microbes and methanogenic microbes, a good source of nutrients and growth substrate should also be combined with the coal. The substrate, nutrients and microbes can be mixed or agglomerated or coated onto the coal particles as they are being stacked into the heap 30. Some good sources of growth substrate materials are biomass from ethanol fermentations, municipal waste sludge, and agricultural waste. These will provide organic material for microbial growth and will also help make the heap anaerobic by consuming oxygen. The more easily degraded organic substrate will stimulate the growth of a large amount of microbes that will cover all the coal particles.

The size range of the coal particles should be determined in laboratory tests to determine the rate of coal to methane conversion as a function of size or surface area to volume. One method of performing these tests is to set up a number of columns each containing different size ranges each mixed with ample nutrient and microbe cultures. The columns are kept anaerobic and the amount of generated methane measured. In addition to columns, small stirred reactors can be used to measure rates of bio-methane generation for much higher surface area to volume ratios then would be used in a large-scale process. The results from this lab test could then be used to estimate rates of methane generation for large-scale field heaps.

This type of testing will allow for optimization of pH, temperature, and other environmental conditions that will be used to model and control a large commercial operation. Models of the system could also be useful to predict and control the rate of methane generation. Several heaps of different size ranges may be constructed to produce methane at different rates as a method of configuring production rates to meet anticipated methane demand.

In this example, a large heap may be constructed nearby an old coal fired power plant that is in the process of converting to a gas-fired power plant. Coal that is brought into the power plant that no longer meets air quality emission standards could be crushed to the experimentally determined size then size separated for one or more heaps or lifts of different size ranges. The finest size range could be agglomerated and stacked in another heap. Each heap or lift will start to produce methane that may supply a gas-fired turbine electricity generator. The cleaner burning coal may continue to be used to generate electric power from the existing coal-fired power plant. In this way the facility could continue to produce as much power as it had before and decrease emissions. This type of change over would also make use of much of the existing facility.

EXAMPLE 4

Peat bogs harbor approximately 30% of the world's soil carbon reserves. The natural biodegradation of peat accounts for 3 to 7% of the global methane emissions. Peat is young coal and the U.S. has the second largest peat resource in the world. The total energy contained in the U.S. peat resources is estimated at the equivalent of about 240 billion barrels of oil. It is evenly distributed throughout the country and is at the surface with little or no overburden.

Peat bogs are generally acidic and anoxic with methanogenic methane production as the major microbiological process. However, the top layer of peat contains methanotrophic microbes that consume much of the methane produced and oxidize it to carbon dioxide and water. The total methane emission from peat bogs is less than 0.1 liters per square meter of surface per day.

Peat can be dewatered and burned for fuel directly. For a number of reasons, including the cost of dewatering, this is not generally done in the U.S., although it is in other parts of the world. In this example, the peat is removed from the bog and made into small pellets or particles to be stacked into the bioreactor. Because of peat's high water content and its soft and compressible nature it should undergo some processing to reduce the compressibility before it is stacked into a heap.

In addition to changing its physical properties, addition of nutrients, pH adjustment and microbial inoculation can be when the heap bioreactor is being formed.

To strengthen the peat particle, a binding agent can be added. Portland cement can function as a binding aid and be used to adjust the pH of the peat. Further, methanogenesis at neutral pH can use a wide range of small organic compounds to produce methane. Thus, laboratory testing of methanogenic methane production can be analyzed as a function of pH, nutrients, and other environmental requirements for the particular peat example. The optimum pH, nutrients, and other conditions may then be adjusted to as the agglomerated particles 14 are produced. In other words, other material 15 and 17 can be agglomerated into the particles 14 to help create the optimum environment and strength of the agglomerated particles 14. In addition to cement, or carbonate rock for strength and pH control biomass or agriculture waste or sludge can be added to provide nutrients and microbes. Alternatively, to provide less compressible particles, the peat may be coated onto a plurality of solid substrates 21, such as coal, oil shale, or rock, as illustrated in FIG. 3.

The resulting peat particles are stacked into a heap 30, as previously described. The heap will start as an aerobic process but will change to an anaerobic process as the oxygen is swept out or consumed. The heap is also covered with an impermeable gas barrier 36 to prevent the introduction of unwanted oxygen. The height of the heap is limited by the compressibility and permeability of the heap particles. The heap must remain permeable enough after it is stacked that liquid can percolate through the heap to bring in nutrients, microbes, and control pH. In addition, it must be gas permeable enough that methane can be removed and oxygen levels controlled.

The rate of methane generation will depend on the microbes ability to ferment the complex peat organic material into acetate, and other simple organic materials. These simple fatty acids and hydrogen and carbon dioxide can be converted into methane. It is anticipated that the rate of methane production should be increased over 10 fold more than the rate of methane generated from peat bogs. Acidic peat bogs produce 6 to 30 g of methane per tonne of peat per day. The heap bioreactor 20 described in this example should, however, be capable of producing more than 300 g of methane per tonne of peat per day.

Although the invention has been described with reference to preferred embodiments and specific examples, it will readily be appreciated by those skilled in the art that many modifications and adaptations of the methods and bioreactors described herein are possible without departure from the spirit and scope of the invention as claimed hereinafter. Thus, it is to be clearly understood that this description is made only by way of example and not as a limitation on the scope of the invention as claimed below.

What is claimed is:

1. A method for producing liquid and gaseous synfuel from carbonaceous material, the method comprising the steps of:
    forming a solid state stacked particle bioreactor with a plurality of particles comprising biodegradable carbonaceous material, the solid state bioreactor having an inter-particle void volume, and the solid state stacked particle bioreactor including a drainage system configured to continuously drain liquid from the stacked particle bioreactor so that the stacked particles are not submerged in a liquid phase;
    inoculating the solid state stacked particle bioreactor with a culture comprising one or more aerobic and/or facultative anaerobic microorganisms capable of fermenting the carbonaceous material;
    fermenting the carbonaceous material in the solid state stacked particle bioreactor to produce alcohol;
    converting the environment within the solid state stacked particle bioreactor from an aerobic environment to an anaerobic environment;
    inoculating the solid state stacked particle bioreactor with a culture comprising one or more anaerobic microorganisms;
    anaerobically bioconverting fermentation products in the stacked particle bioreactor to gaseous synfuel; and
    collecting alcohol and gaseous synfuel from the solid state stacked particle bioreactor.

2. The method of claim 1, further comprising the step of providing a gas impermeable barrier over the stacked particles.

3. The method of claim 1, wherein the produced alcohol is collected via a liquid collection system.

4. The method of claim 1, wherein the produced gaseous synfuel is collected via a gas collection system.

5. The method of claim 1, wherein the carbonaceous material is selected from the group consisting of oil sands, carbonaceous rock, asphalt, asphaltic oil, waste oil, bitumen, tar, pitch, kerogen, rubber, and agricultural waste.

6. The method of claim 5, wherein the carbonaceous material comprises agricultural waste.

7. The method of claim 1, wherein the inter-particle void volume is greater than or equal to about 15% of the total volume of the bioreactor.

8. The method of claim 1, wherein the inter-particle void volume is greater than or equal to about 20% of the total volume of the bioreactor.

9. The method of claim 1, wherein the inter-particle void volume is in the range of about 20%-35% of the total volume of the bioreactor.

10. The method of claim 1, wherein the step of inoculating the solid state stacked particle bioreactor with a culture comprising one or more aerobic and/or facultative anaerobic microorganisms is performed as the plurality of particles are being stacked to form the bioreactor.

11. The method of claim 1, further comprising agglomerating the particles together to form agglomerates having a particle size in the range of 0.3 cm to 2.54 cm prior to the forming step.

12. The method of claim 1, further comprising mixing a plurality of substrates having a particle size greater than or equal to about 0.3 cm with the particles prior to the forming step.

13. The method of claim 1, wherein the step of forming a solid state stacked particle reactor includes providing an irrigation system in proximity to the top of the solid state stacked particle bioreactor.

14. The method of claim 13, wherein the step of forming a solid state stacked particle bioreactor includes burying a plurality of emitters in the top of the solid state stacked particle bioreactor.

15. The method of claim 14, wherein at least one of the buried emitters is configured to be independently controlled.

16. The method of claim 2, wherein the gas impermeable barrier comprises a clay barrier layer.

17. The method of claim 2, wherein the gas impermeable barrier comprises a plastic liner.

18. The method of claim 1, wherein the converting step includes purging oxygen from the solid state stacked particle bioreactor.

19. The method of claim 18, wherein the solid state stacked particle bioreactor is purged with a gas selected from the group consisting of argon, nitrogen, carbon dioxide, ammonia, and hydrogen.

20. The method of claim 1, wherein the forming step includes providing a gas delivery system for the solid state stacked particle bioreactor.

21. The method of claim 20, wherein the gas delivery system is in communication with a bottom portion of the solid state stacked particle bioreactor.

22. The method of claim 1, further comprising the step of purifying the collected gaseous synfuel.

23. The method of claim 1, further comprising the step of providing a plurality of oxygen sensors throughout the solid state stacked particle bioreactor.

24. A method for producing both liquid and gaseous synfuel from carbonaceous material, the method comprising the steps of:

forming a solid state bioreactor with a plurality of particles comprising biodegradable carbonaceous material, an inoculum comprising one or more aerobic and/or facultative anaerobic microorganisms, and inert substrates, the solid state bioreactor having an inter-particle void volume, and the solid state stacked particle bioreactor including a drainage system configured to continuously drain liquid from the stacked particle bioreactor so that the stacked particles are not submerged in a liquid phase;

fermenting the carbonaceous material within the solid state bioreactor with the aerobic microbial consortium to produce fermentation products comprising alcohol;

providing an anaerobic environment within the solid state bioreactor following the fermentation; and anaerobically bioconverting fermentation products to gaseous synfuel, wherein the substrates maintain the inter-particle void volume during the fermentation and anaerobic bioconversion steps above a predetermined level.

* * * * *